(12) United States Patent
Mukai et al.

(10) Patent No.: US 10,137,258 B2
(45) Date of Patent: Nov. 27, 2018

(54) PHARMACEUTICAL INJECTION DEVICE AND STORAGE CASE THEREFOR

(71) Applicant: PHC HOLDINGS CORPORATION, Tokyo (JP)

(72) Inventors: Yasutaka Mukai, Ehime (JP); Kenji Murakami, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 118 days.

(21) Appl. No.: 14/773,183

(22) PCT Filed: Mar. 7, 2014

(86) PCT No.: PCT/JP2014/001311
§ 371 (c)(1),
(2) Date: Sep. 4, 2015

(87) PCT Pub. No.: WO2014/136462
PCT Pub. Date: Sep. 12, 2014

(65) Prior Publication Data
US 2016/0015910 A1    Jan. 21, 2016

(30) Foreign Application Priority Data

Mar. 8, 2013   (JP) .................................. 2013-046323
Nov. 13, 2013  (JP) .................................. 2013-235395

(51) Int. Cl.
*A61M 5/50*      (2006.01)
*A61M 5/00*      (2006.01)
(Continued)

(52) U.S. Cl.
CPC .......... *A61M 5/5086* (2013.01); *A61M 5/002* (2013.01); *A61M 5/20* (2013.01);
(Continued)

(58) Field of Classification Search
CPC ...... A61M 5/5086; A61M 5/002; A61M 5/20; A61M 5/34; A61M 5/50; A61M 5/24;
(Continued)

(56) References Cited

U.S. PATENT DOCUMENTS

2005/0090781 A1    4/2005   Baba et al.
2011/0218502 A1    9/2011   Iio et al.
(Continued)

FOREIGN PATENT DOCUMENTS

CN         1602212 A      3/2005
CN        102202703 A     9/2011
(Continued)

OTHER PUBLICATIONS

Extended European Search Report issued in Patent Application No. EP 14 76 0431.8 dated Mar. 14, 2016.
(Continued)

*Primary Examiner* — Andrew Perreault
(74) *Attorney, Agent, or Firm* — Pearne & Gordon LLP

(57) ABSTRACT

The present invention relates to a pharmaceutical injection device, and it is an object thereof to prompt the user to replace the injection needle as needed. To achieve this object, the present invention is configured such that a needle detector switch 8 that directly or indirectly detects the mounting of an injection needle to a pharmaceutical syringe 5 is provided to a main case 2, this needle detector switch 8 is connected to a controller 21, and the controller 21 displays on a display component 19 an injection needle removal message that directly or indirectly prompts the user to remove an injection needle 6 from the pharmaceutical syringe 5 when the mounting of the injection needle 6 to the pharmaceutical syringe 5 has been detected by the needle detector switch 8 in the switching off the a power switch 16.

11 Claims, 25 Drawing Sheets

(51) Int. Cl.
    *A61M 5/20*     (2006.01)
    *A61M 5/34*     (2006.01)
    *A61M 5/24*     (2006.01)

(52) U.S. Cl.
    CPC ........... *A61M 5/34* (2013.01); *A61M 5/50* (2013.01); *A61M 5/24* (2013.01); *A61M 2005/2414* (2013.01); *A61M 2205/14* (2013.01); *A61M 2205/18* (2013.01); *A61M 2205/276* (2013.01)

(58) Field of Classification Search
    CPC ...... A61M 2205/60; A61M 2205/6063; A61M 2205/6036; A61M 2005/2414; A61M 2205/14; A61M 2205/18; A61M 2205/276
    USPC .................................. 206/570, 571; 604/189
    See application file for complete search history.

(56) References Cited

U.S. PATENT DOCUMENTS

| | | | |
|---|---|---|---|
| 2011/0238017 A1* | 9/2011 | Watanabe | A61M 5/14546 604/189 |
| 2011/0257602 A1 | 10/2011 | Watanabe et al. | |
| 2012/0004637 A1 | 1/2012 | Krulevitch et al. | |
| 2013/0172819 A1 | 7/2013 | Iio et al. | |

FOREIGN PATENT DOCUMENTS

| | | |
|---|---|---|
| CN | 102256644 A | 11/2011 |
| CN | 102413759 A | 4/2012 |
| EP | 2319562 A1 | 5/2011 |
| EP | 2 357 013 A1 | 8/2011 |
| EP | 2361647 A1 | 8/2011 |
| EP | 2641626 A1 | 9/2013 |
| JP | 2007-313372 A | 12/2007 |
| JP | 2012-519027 A | 8/2012 |
| WO | 2010055608 A1 | 5/2010 |
| WO | 2010/073452 A1 | 7/2010 |
| WO | 2010/098929 A1 | 9/2010 |
| WO | 2012/066767 A1 | 5/2012 |
| WO | 2012/160160 A1 | 11/2012 |

OTHER PUBLICATIONS

Japanese Office Action for Application No. 2015-504187 dated Jun. 21, 2016.
International Search Report for Application No. PCT/JP2014/001311 dated Jun. 10, 2014.
Chinese Office Action issued in Patent Application No. CN 201480011509 dated Jan. 3, 2017.

* cited by examiner

PHARMACEUTICAL INJECTION DEVICE AND STORAGE CASE THEREFOR

TECHNICAL FIELD

The present invention relates to a pharmaceutical injection device for injecting insulin, growth hormones, or other such pharmaceuticals, and to a storage case for the same.

BACKGROUND ART

A conventional pharmaceutical injection device of this type comprises a main case that has a pharmaceutical syringe mounting component, a piston that is provided movably with respect to the pharmaceutical syringe mounted to the pharmaceutical syringe mounting component, a driver that drives this piston, a controller that is electrically connected to this driver, a display component that is electrically connected to this controller, and a power switch. With this configuration, a needle detector switch that detects the state of mounting of an injection needle to a pharmaceutical syringe is provided to the main case, and this needle detector switch is connected to the controller (see Patent Literature 1, for example).

CITATION LIST

Patent Literature

Patent Literature 1: WO 2012/066767

SUMMARY

Technical Problem

In a conventional example, since the mounting of an injection needle to a pharmaceutical syringe can be detected, the user will not forget to mount the injection needle when it is time for a pharmaceutical injection.

However, even with this conventional example, there is no reminder about removing the injection needle from the pharmaceutical syringe, and as a result, the injection needle that was used in the previous injection may end up being used again the next time, so there has been a need for improvement in this regard.

That is, an injection needle that has already been used is preferably not used again the next time, and this is the area in which improvement was needed.

In view of this, it is an object of the present invention to provide a pharmaceutical injection device with which the user can be prompted to use the device properly, as well as a storage case for the same.

Solution to Problem

To achieve the stated object, the present invention comprises a main case, a piston, a driver, a power switch, a display component, a needle detector, and a controller. The main case has a pharmaceutical syringe mounting component to which a pharmaceutical syringe is mounted. The piston is provided movably with respect to the pharmaceutical syringe mounted to the pharmaceutical syringe mounting component. The driver drives the piston. The power switch switches power on and off. The display component is provided to the main case. The needle detector directly or indirectly detects the mounting of an injection needle. The controller displays on the display component a message directly or indirectly prompting the user to remove the injection needle when the mounting of the injection needle has been detected by the needle detector in the switching off of the power switch.

Specifically, with the present invention, the controller causes the display component to display a message directly or indirectly prompting the user to remove the injection needle when the mounting of the injection needle has been detected by the needle detector in the switching off of the power switch.

Consequently, the used injection needle is removed and when it is time for the next pharmaceutical injection, a new injection needle is mounted to the pharmaceutical syringe, and the pharmaceutical injected.

Advantageous Effects

With the pharmaceutical injection device and the storage case of the present invention, it is possible to encourage proper use.

DESCRIPTION OF EMBODIMENTS

Embodiments of the present invention will now be described through reference to the appended drawings.
Embodiment 1
1. Configuration
1-1. External Configuration of Pharmaceutical Injection Device 101

Figure 1:
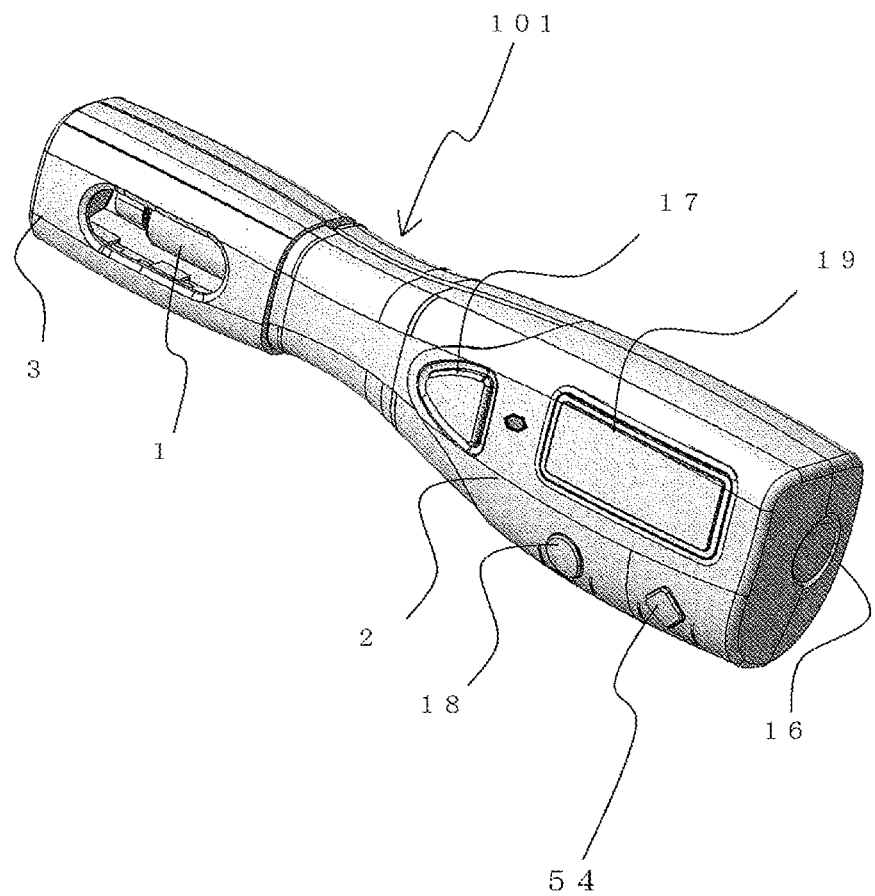
FIG. 1 is an oblique view of the pharmaceutical injection device in Embodiment 1 pertaining to the present invention.
Figure 2:
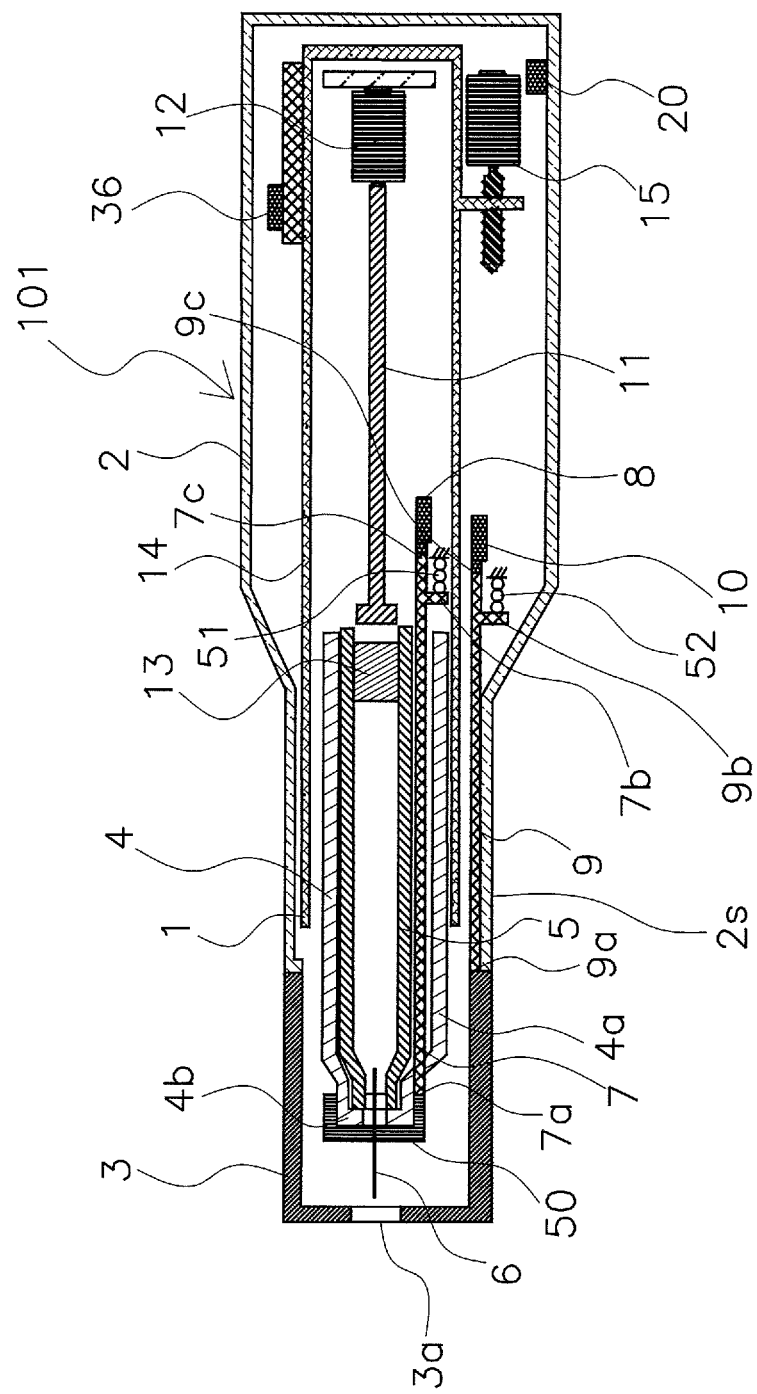
FIG. 2 is a cross section of the pharmaceutical injection device shown in FIG. 1.

FIG. 1 is an oblique view of a pharmaceutical injection device 101 of Embodiment 1. FIG. 2 is a simplified cross section of the pharmaceutical injection device 101 in Embodiment 1.

As shown in FIGS. 1 and 2, the pharmaceutical injection device 101 in this embodiment comprises a main case 2 that is substantially cylindrical and has a pharmaceutical syringe mounting component 1 on the distal end side, and a cap 3 that is detachably provided to the outer peripheral part of the pharmaceutical syringe mounting component 1 of this main case 2. In the following description, the side on which the cap 3 is disposed shall be referred to as the distal end side or the front side, and the opposite side (the side on which a power switch 16 (discussed below) is provided) as the rear end side.

A power switch 16, a pharmaceutical injection switch 17, an air vent switch 18, and so forth are provided on the outside of the main case 2.

The power switch 16 is for turning on or off the power to the pharmaceutical injection device 101, and is provided to the end face on the opposite side of the main case 2 from the cap 3. The pharmaceutical injection switch 17 is provided to a side face of the main case 2, and a pharmaceutical injection operation is performed by pressing the pharmaceutical injection switch 17. A display component 19 is provided on the rear end side of the pharmaceutical injection switch 17, and displays various messages such as measurement results. The air vent switch 18 is provided along the lower side of the display component 19 in FIG. 1, and an air vent operation is performed by pressing the air vent switch 18.

1-2. Internal Configuration of Pharmaceutical Injection Device 101

As shown in FIG. 2, a syringe cover 4 is provided to the pharmaceutical syringe mounting component 1. A pharmaceutical syringe 5 is disposed inside this syringe cover 4, and a needle mounting component 4b to which an injection needle 6 is mounted is provided on the distal end side of the syringe cover 4.

Before this syringe cover 4 is attached to the pharmaceutical syringe mounting component 1, the pharmaceutical syringe 5 is set inside this syringe cover 4, and then the injection needle 6 is mounted to the needle mounting component 4b on the distal end side of the syringe cover 4, resulting in a state in which the injection needle 6 has been mounted to the pharmaceutical syringe 5. More precisely, the injection needle 6 is fixed to an attachment component 50, and the attachment component 50 is threaded onto the needle mounting component 4b, thereby mounting the injection needle 6 to the syringe cover 4.

Thus, in a state in which the pharmaceutical syringe 5 has been mounted to the pharmaceutical syringe mounting component 1, as shown in FIGS. 1 and 2, the cap 3 is mounted in front of the main case 2 at the outer periphery of the pharmaceutical syringe mounting component 1.

The mounting of the injection needle 6 to the pharmaceutical syringe 5 is directly detected by a needle detector switch 8 in the main case 2 via a lever 7.

More precisely, the syringe cover 4 has an outer tube 4a that covers the outside of the pharmaceutical syringe 5, and the lever 7, which is disposed on the inside of the outer tube 4a and along the outer tube 4a, going from the distal end toward the rear end.

The distal end 7a of the lever 7 protrudes from the outer tube 4a to the distal end side. Also, a protrusion 7b is formed at the portion of the lever 7 that is to the rear of the outer tube 4a. A biasing component 51 such as a spring is provided that biases the protrusion 7b to the distal side in a state in which the syringe cover 4 has been attached to the pharmaceutical syringe mounting component 1. The entire lever 7 is biased by this biasing component 51 to the distal end side with respect to the outer tube 4a. The needle detector switch 8 is disposed on the rear side of the rear end 7c of the lever 7 in a state in which the syringe cover 4 has been attached to the pharmaceutical syringe mounting component 1.

When the attachment component 50 is attached to the needle mounting component 4b, the distal end 7a of the lever 7 is pushed to the rear end side by the attachment component 50, and the lever 7 is pushed against the biasing force of the biasing component 51 to the rear end side. The movement of the lever 7 to the rear end side causes the rear end 7c of the lever 7 to press the needle detector switch 8, putting the needle detector switch 8 in its on state, and the mounting of the injection needle 6 is detected.

Also, the mounting of the cap 3 to the main case 2 is detected by a cap detector switch 10 in the main case 2 via a lever 9. More precisely, the lever 9 is disposed along the distal end portion of the outer wall 2s of the main case 2, on the inside thereof. A protrusion 9b is formed near the rear end 9c of the lever 9. A biasing component 52 that biases this protrusion 9b to the distal end side is provided. The entire lever 9 is biased by the biasing component 52 to the distal end side with respect to the main case 2. The cap detector switch 10 is disposed on the rear end side of the rear end 9c of the lever 9.

When the cap 3 is mounted, the cap 3 pushes the distal end 9a to the rear end side, and the lever 9 is pushed to the rear end side against the biasing force of the biasing component 52. This movement of the lever 9 to the rear end side causes the rear end 9c of the lever 9 to press the cap detector switch 10, putting the cap detector switch 10 in its on state, and the mounting of the cap 3 to the main case 2 is detected.

Also, a piston 11 is provided to the rear of the pharmaceutical syringe 5 in the main case 2, and this piston 11 is driven by a piston drive motor 12. Consequently, a gasket 13 in the pharmaceutical syringe 5 is pushed forward, which causes the pharmaceutical to be pushed out of the pharmaceutical syringe 5 through the injection needle 6.

In this embodiment, a moving member 14 is provided that houses the piston 11, the piston drive motor 12, and the rear outer periphery of the syringe cover 4, and this moving member 14 is configured so that it is driven forward and backward by a needle insertion and withdrawal drive motor 15.

That is, from the state in FIG. 2, when the needle insertion and withdrawal drive motor 15 is driven, the injection needle 6 moves forward along with the moving member 14, and as a result, the injection needle 6 protrudes forward through the distal end opening 3a of the cap 3, and thereby pierces the skin.

When the piston drive motor 12 is then driven, the piston 11 moves the gasket 13 forward, the result being that the pharmaceutical in the pharmaceutical syringe 5 is injected into the body through the injection needle 6.

In order to perform the above operation, the power switch 16, the pharmaceutical injection switch 17, the air vent switch 18, the display component 19, and a charging terminal 20 are provided to the outer peripheral face of the main case 2 as discussed above (shown in FIG. 1).

1-3. Control Configuration of Pharmaceutical Injection Device 101

Figure 3:
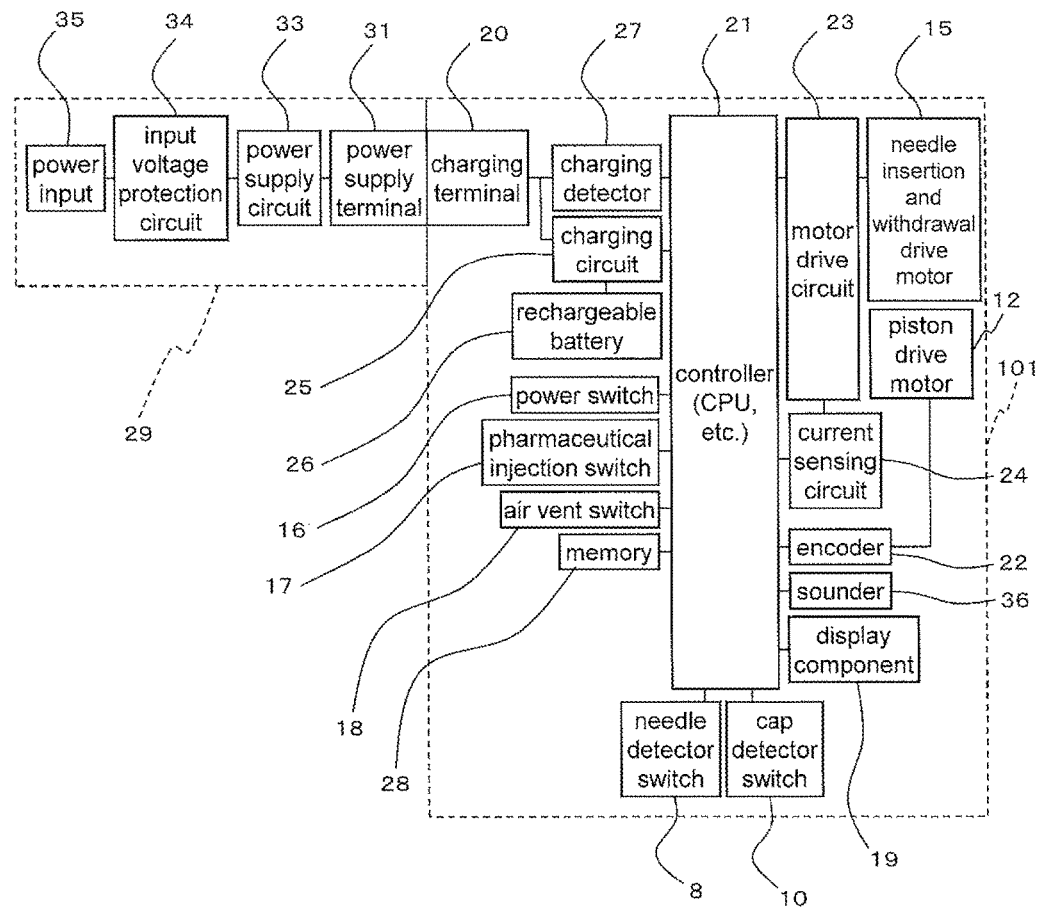
FIG. 3 is a control block diagram showing the simplified electrical configuration of the pharmaceutical injection device shown in FIG. 1 and its storage case.

FIG. 3 is a block diagram showing the control configuration of the pharmaceutical injection device 101 in this embodiment.

As shown in FIG. 3, the needle detector switch 8, the cap detector switch 10, the piston drive motor 12, the needle insertion and withdrawal drive motor 15, the power switch 16, the pharmaceutical injection switch 17, the air vent switch 18, the display component 19, and the charging terminal 20 are connected to a controller 21.

Of these, the piston drive motor 12 is connected to the controller 21 via an encoder 22.

Also, the piston drive motor 12 and the needle insertion and withdrawal drive motor 15 are connected to the controller 21 via a motor drive circuit 23.

The motor drive circuit 23 is connected to the controller 21 via a current sensing circuit 24.

The charging terminal 20 is connected to a rechargeable battery 26 via a charging circuit 25.

The charging terminal 20 is connected to the controller 21 via a charging detector 27.

Similarly, the charging circuit 25 is also connected to the controller 21.

Furthermore, a memory 28 that stores control programs and the like is connected to the controller 21.

1-4. Storage Case 29

Figure 4:
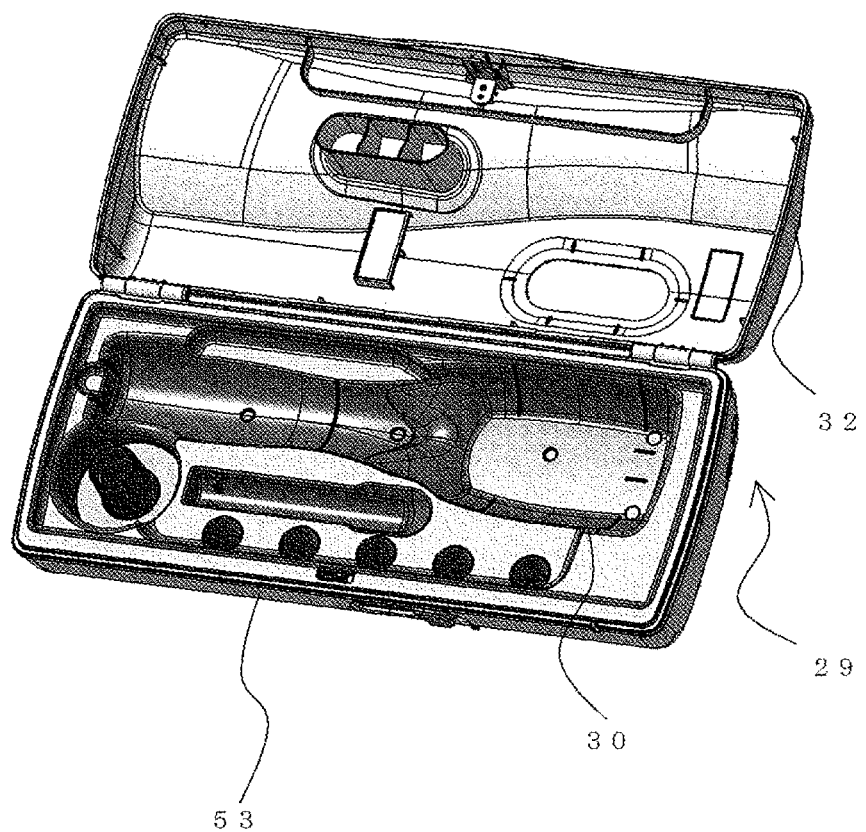
FIG. 4 is an oblique view of a storage case for storing the pharmaceutical injection device shown in FIG. 1.
Figure 5:
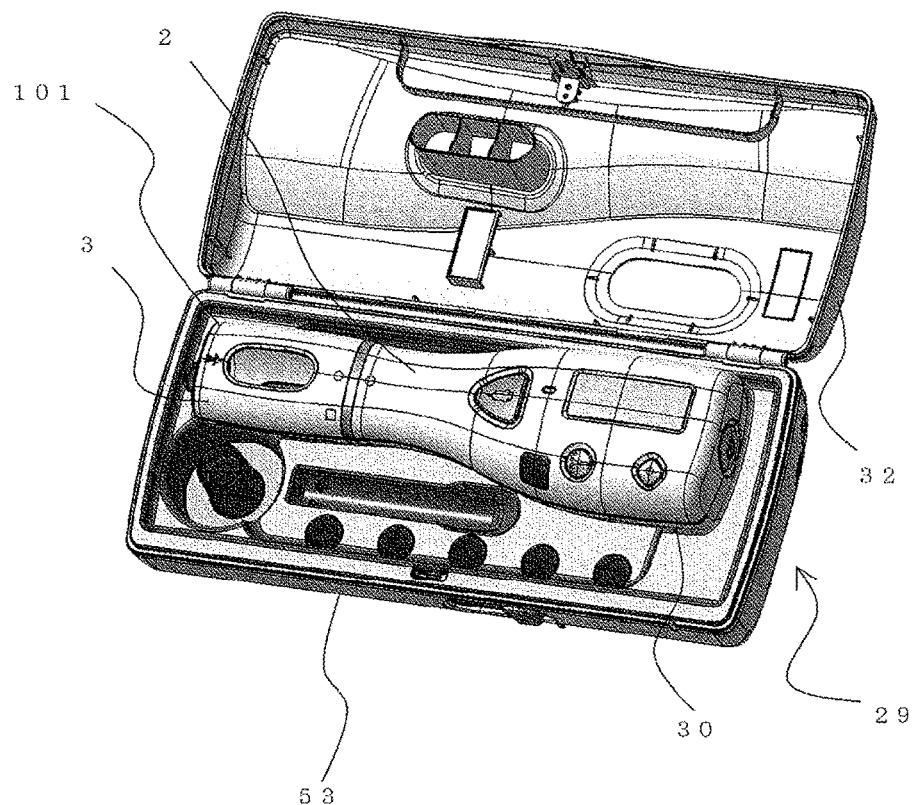
FIG. 5 is an oblique view of the state when the pharmaceutical injection device shown in FIG. 1 has been put into its storage case.
Figure 6:
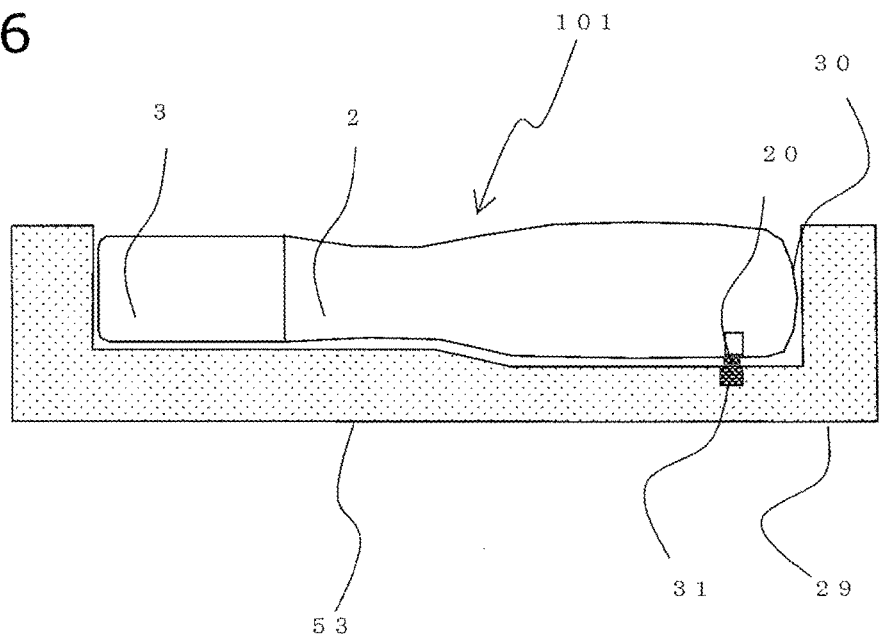
FIG. 6 is a cross section showing the state in FIG. 5 in simplified form.

FIG. 4 is an oblique view of a storage case 29 used to store the pharmaceutical injection device 101 of Embodiment 1. FIG. 5 is an oblique view of the state when the pharmaceutical injection device 101 has been put into the storage case 29 shown in FIG. 4. FIG. 6 is a cross section showing the pharmaceutical injection device 101 and the storage case 29 in simplified form.

The pharmaceutical injection device 101 configured as above is stored in the storage case 29 shown in FIGS. 4 and 5, and the charging of the rechargeable battery 26 is also performed during this storage.

More specifically, as shown in FIG. 4, the storage case 29 has a placement component 53 in which is formed a mounting recess 30 in which the main case 2 of the pharmaceutical injection device 101 is mounted, and a lid 32. The mounting recess 30 is formed in a shape that conforms to the outer shape of the pharmaceutical injection device 101 in a state in which the cap 3 has been attached to the main case 2. As shown in FIG. 6, a power supply terminal 31 is provided on the bottom face of the mounting recess 30. When the main case 2 is mounted in the mounting recess 30, as shown in FIG. 6, the power supply terminal 31 provided to the mounting recess 30 comes into contact with the charging terminal 20 of the main case 2, and the rechargeable battery 26 is charged.

In for the pharmaceutical injection device 101 to be stored in the storage case 29 during charging, in the state shown in FIG. 5, the lid 32 is closed and mated with the placement component 53 so as to cover the mounting recess 30 and the pharmaceutical injection device 101.

As shown in FIG. 3, the power supply terminal 31 is connected to a power input 35 via a power supply circuit 33 and an input voltage protection circuit 34. This power input 35 has a plug or the like that can be plugged into a wall outlet or the like.

2. Operation

Figure 7A:
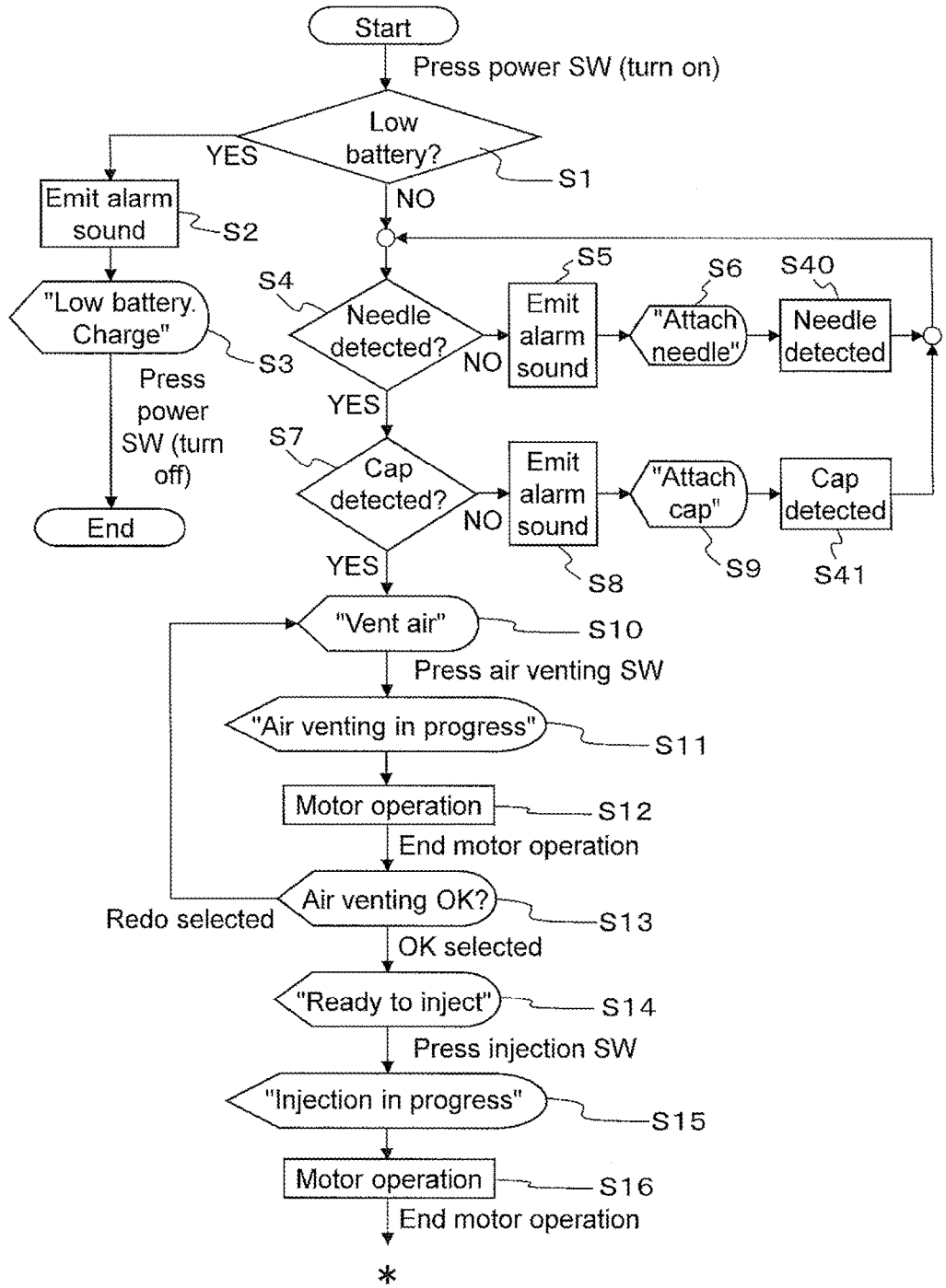
FIG. 7A is a flowchart of the operational control of the pharmaceutical injection device shown in FIG. 1.
Figure 7B:
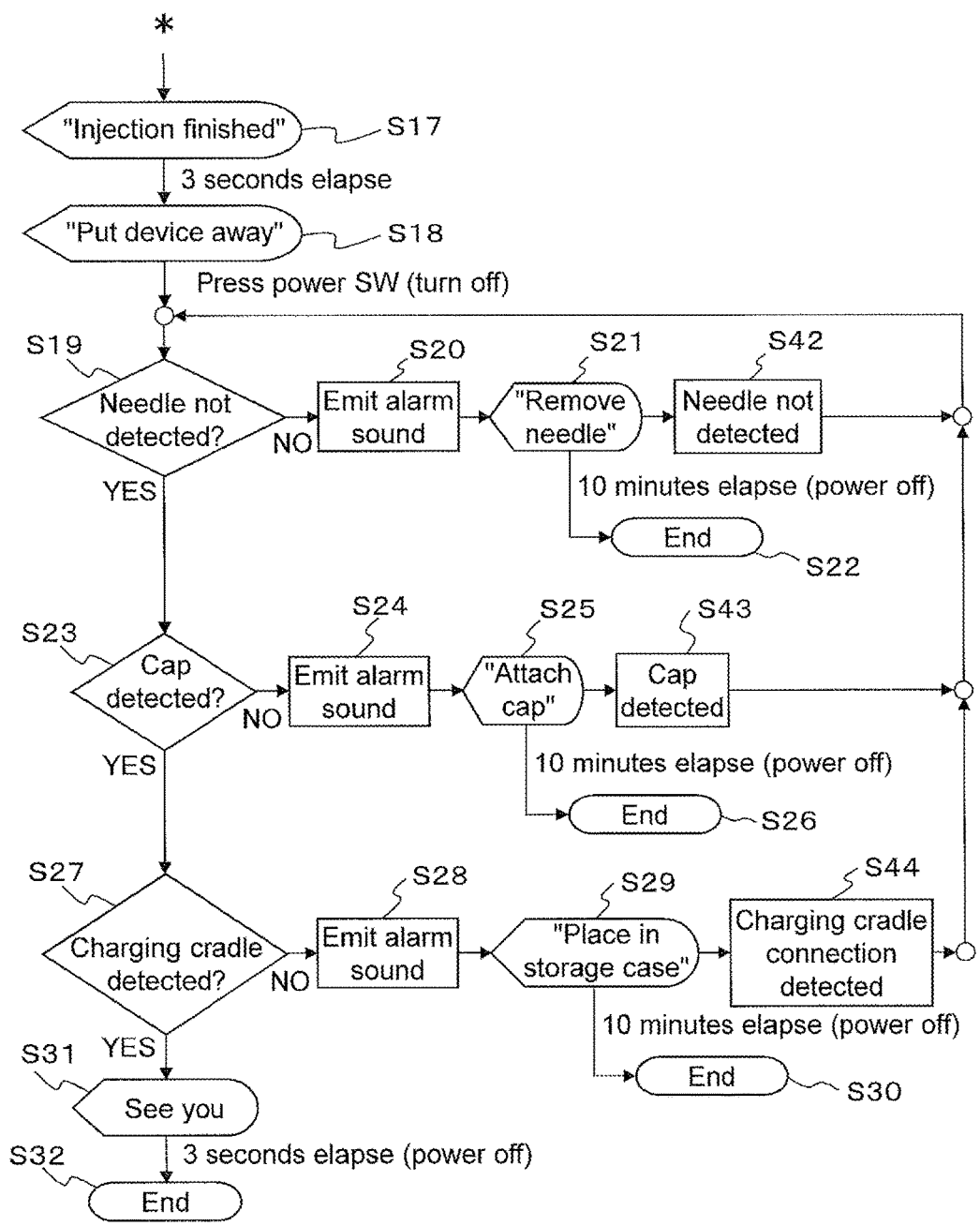
FIG. 7B is a flowchart of the operational control of the pharmaceutical injection device shown in FIG. 1.

FIGS. 7A and 7B are flowcharts of the operation of the pharmaceutical injection device 101 in Embodiment 1.

With the above configuration, when a pharmaceutical is injected, the pharmaceutical injection device 101 is as shown in FIGS. 1 and 2, in which the pharmaceutical syringe 5 is mounted to the pharmaceutical syringe mounting component 1 of the main case 2, and the injection needle 6 is also mounted and the outer periphery thereof is covered with by the cap 3.

In this state, first the power switch 16 (labeled power SW in FIGS. 7A and 7B) is pressed and put in its on state.

The controller 21 then detects the voltage of the rechargeable battery 26 via the charging circuit 25 (51 in FIG. 7A).

If the voltage of the rechargeable battery 26 is low, the controller 21 emits an alarm sound from a sounder 36 connected to the controller 21 shown in FIG. 3 (S2 in FIG. 7A), and then a message prompting the user to charge the battery, because the charge is low, is displayed on the display component 19 (S3 in FIG. 7A). More specifically, a message of "Low battery. Charge." is displayed on the display component 19. After the message is displayed, the user presses the power switch 16 to shut off the power, and control is ended.

Also, when the rechargeable battery 26 is at the appropriate voltage level, first the needle detector switch 8 detects whether or not the injection needle 6 has been mounted (S4 in FIG. 7A).

If the injection needle 6 is determined to have not been mounted, an alarm sound is emitted from the sounder 36 (S5 in FIG. 7A), and then a message prompting the user to mount the injection needle 6 is displayed on the display component 19 (S6 in FIG. 7A).

In other words, a direct message that prompts the user to mount the injection needle 6 is displayed on the display component 19 as "Attach needle" (S6 in FIG. 7A). In the state in S6, the system waits until the mounting the injection needle 6 is detected, and detection of the mounting of the injection needle 6 (S40) triggers the control to move to S4.

Next, the cap detector switch 10 detects whether or not the cap 3 has been mounted to the pharmaceutical syringe mounting component 1 of the main case 2 so as to cover the pharmaceutical syringe 5 and the injection needle 6 as shown in FIG. 2 (S7 in FIG. 7A).

Then, if the cap 3 is determined not to have been mounted, an alarm sound is emitted from the sounder 36 (S8 in FIG. 7A), and then a message prompting the user to mount the cap 3 is displayed on the display component 19 (S9 in FIG. 7A). More specifically, a message of "Attach cap" is displayed on the display component 19. After the display, the system waits until the mounting of the cap 3 is detected in the state of S9, and detection of the mounting of the cap 3 (S41) triggers the control to move to S4. Control thus returns to S4. That is, when the mounting of the needle and the mounting of the cap are detected, control proceeds to S10.

After this, the controller 21 causes the display component 19 to give a display prompting the user to perform an air venting operation (S10 in FIG. 7A).

At this point, when the user presses the air vent switch 18 shown in FIG. 1, the display component 19 gives a display of "Air venting in progress" (S11 in FIG. 7A). Next, the needle insertion and withdrawal drive motor 15 is driven, which causes the injection needle 6 to protrude from the distal end opening of the cap 3. In this state, the piston drive motor 12 is then driven, which causes the gasket 13 to be pushed by the piston 11, and as a result a small amount of pharmaceutical is ejected from the distal end of the injection needle 6, and air venting is performed. It is possible to confirm the air venting by visually checking the ejection of the pharmaceutical.

Then, when this air venting operation is complete, the needle insertion and withdrawal drive motor 15 is reversed, putting the injection needle 6 in a state of being housed in the cap 3 as shown in FIG. 2 (S12 in FIG. 7A).

After this, the controller 21 causes the display component 19 to display whether the air venting is complete (OK key). More specifically, an "OK" key and "Redo" key are displayed on the display component 19 along with the message of "Has air been vented?" For example, as shown in FIG. 1, a selector switch 54 is disposed next to the air vent switch 18, the "OK" key is selected with this selector switch 54, and the air vent switch 18, etc., is pressed to enter the "OK" key.

If this OK key is operated, the controller 21 then displays on the display component 19 that the device is ready for injection (S13 and S14 in FIG. 7A). More specifically, the controller 21 displays "Ready to inject" on the display component 19.

The user then places the distal end opening 3a of the cap 3 (see FIG. 2) against the pharmaceutical administration site (specifically, the skin)

If the pharmaceutical injection switch 17 is then operated, the controller 21 first causes the display component 19 to display "Injection in progress" (S15 in FIG. 7A). Next, the needle insertion and withdrawal drive motor 15 is operated so that the injection needle 6 pierces pharmaceutical administration site through the distal end opening portion 3a of the cap 3.

Next, the piston drive motor 12 moves the piston 11 to the distal end side and pushes the gasket 13, which causes the pharmaceutical in the pharmaceutical syringe 5 to be injected into the body through the injection needle 6.

Once the injection is finished, the piston drive motor 12 and needle insertion and withdrawal drive motor 15 are reversed. As a result, the injection needle 6 goes back inside the cap 3, and the piston 11 is pulled out of the pharmaceutical syringe 5 (S16 in FIG. 7A).

The controller 21 then causes the display component 19 to display that the pharmaceutical injection is finished (S17 in FIG. 7B). More specifically, a message of "Injection finished" is displayed on the display component 19. After three seconds this display, the controller 21 causes the display component 19 to display a message prompting the user to put the device away (S18 in FIG. 7B). More specifically, a message of "Put device away" is displayed on the display component 19.

Upon seeing this display, the user performs an operation to turn off the power switch 16, and when this operation is performed, first the controller 21 uses the needle detector switch 8 to detect whether or not the injection needle 6 is still mounted to the pharmaceutical syringe 5 (S19 in FIG. 7B).

If the presence of the injection needle 6 has been confirmed by the needle detector switch 8, an alarm sound is emitted from the sounder 36 connected to the controller 21 shown in FIG. 3 (S20 in FIG. 7B), and the controller 21 causes the display component 19 to display a message prompting the user to remove of the injection needle 6 (S21 in FIG. 7B). More specifically, a message of "Remove needle" is displayed on the display component 19.

After this, if the removal of the injection needle 6 is not executed for at least 10 minutes, the controller 21 switches off the power to prevent unintended consumption of rechargeable battery 26 (S22 in FIG. 7B). On the other hand, if the removal of the injection needle 6 is executed within 10 minutes, the injection needle 6 is not detected by the needle detector switch 8 (S42 in FIG. 7B). If the injection needle 6 is thus undetected, control proceeds to S19.

In S19, if the injection needle 6 is an undetected state, the controller 21 then uses the cap detector switch 10 to detect whether or not the cap 3 has been mounted to the pharmaceutical syringe mounting component 1 of the main case 2 (S23 in FIG. 7B).

That is, as shown in FIG. 5, the mounting state of the cap 3 is detected for the purpose of preventing the cap 3 from being lost, by storing the cap 3 along with the main case 2 in the mounting recess 30 of the storage case 29.

Therefore, in S23, if the presence of the cap 3 is not detected by the cap detector switch 10, and the cap 3 has not been attached to the pharmaceutical syringe mounting component 1 of the main case 2, an alarm sound is emitted from the sounder 36 connected to the controller 21 shown in FIG. 3 (S24 in FIG. 7B). The controller 21 then causes the display component 19 to give a display prompting the user to mount of the cap 3 (S25 in FIG. 7B). More specifically, a message of "Attach cap" is displayed on the display component 19.

After this, if the mounting of the cap 3 is not executed for at least 10 minutes, the controller 21 switches off the power to prevent unintended consumption of rechargeable battery 26 (S26 in FIG. 7B). On the other hand, if the mounting of the cap 3 is executed within 10 minutes, the mounting of the cap 3 is detected by the cap detector switch 10 (S43 in FIG. 7B). When the mounting of the cap 3 is detected, control proceeds to S19.

In S23, when the mounting of the cap 3 is confirmed, the controller 21 then checks the charge state with the charging detector 27, thereby detecting whether or not the main case 2 has been set in the mounting recess 30 of the storage case 29 as shown in FIG. 5 (S27 in FIG. 7B).

That is, when the main case 2 is set in the mounting recess 30 of the storage case 29, charging is started when the charging terminal 20 and the power supply terminal 31 enter a conductive state, so by detecting this conductive state the controller 21 detects that the main case 2 has been set in the mounting recess 30 of the storage case 29.

Then, in S27, if the charging detector 27 has not detected the start of charging, an alarm sound is emitted from the sounder 36 connected to the controller 21 shown in FIG. 3 (S28 in FIG. 7B). The controller 21 then causes the display component 19 to give a display prompting the user to set the main case 2 in the mounting recess 30 of the storage case 29 (S29 in FIG. 7B). More specifically, a message of "Place in storage case" is displayed on the display component 19.

After this, if the setting of the main case 2 in the mounting recess 30 of the storage case 29 is not executed for at least 10 minutes, the controller 21 switches off the power to prevent unintended consumption of rechargeable battery 26 (S30 in FIG. 7B). On the other hand, if the setting of the main case 2 in the mounting recess 30 of the storage case 29 is executed within 10 minutes, the start of charging is detected by the charging detector 27 (S44 in FIG. 7B). When the start of charging is detected, control proceeds to S19.

Also, in S27, if it is detected that the main case 2 has been set in the mounting recess 30 of the storage case 29, the controller 21 causes the display component 19 to display that the appropriate action was taken (S31 in FIG. 7B), and then turns off the power (S32 in FIG. 7B). In S31, specifically, the display component 19 displays a message of "See you."

Although not shown in FIG. 7B, in S21, S25, and S29, an operation confirmation sound may be emitted for notifying the user that the appropriate action has been taken. In this case, the operation confirmation sound preferably as a different sound quality or rhythm from that of the alarm sound notification (S20, S24, S28), so as to distinguish the alarm sound from the operation confirmation sound.

3. Key Features (3-1)

As shown in FIG. 2, the pharmaceutical injection device 101 in this embodiment comprises the main case 2, the piston 11, the piston drive motor 12 (an example of a driver), the power switch 16, the display component 19, the needle detector switch 8 (an example of a needle detector), and the controller 21. The main case 2 has the pharmaceutical syringe mounting component 1 to which the pharmaceutical syringe 5 is mounted. The piston 11 is provided movably relative to the pharmaceutical syringe 5 mounted to the pharmaceutical syringe mounting component 1. The piston drive motor 12 drives the piston 11. The power switch 16 switches the power on or off. The display component 19 is provided in the main case 2. The needle detector switch 8 directly detects the mounting state of the injection needle 6. The controller 21, as shown in FIGS. 7A and 7B, executes first control in which a message directly prompting the user to remove the injection needle 6 is displayed on the display component 19 when the needle detector switch 8 has detected the mounting of the injection needle 6 in the switching off of the power switch 16 (S19, S21).

Thus, the mounting state of the injection needle 6 during the switching off of the power switch 16 is checked, and if it is detected that the injection needle 6 has been mounted, a message to remove the injection needle 6 is displayed.

Consequently, the user can be prompted to remove the injection needle 6 and store the pharmaceutical injection device 101 in the storage case 29, so the user will be less apt to forget to remove the injection needle 6 when putting the device away.

Therefore, an injection needle 6 that has been used once will be less likely to be reused.

(3-2)

As shown in FIG. 2, the pharmaceutical injection device 101 in this embodiment detects the mounting state of the injection needle 6 via the lever 7.

The lever 7 moves when the injection needle 6 is mounted, this movement of the lever 7 is detected by the needle detector switch 8, and the mounting state of the injection needle 6 is detected.

(3-3)

As shown in FIG. 2, with the pharmaceutical injection device 101 in this embodiment, the pharmaceutical syringe 5 is inserted into the syringe cover 4 and mounted to the pharmaceutical syringe mounting component 1, and the needle mounting component 4b to which the injection needle 6 is mounted is provided to the distal end of the syringe cover 4. The injection needle 6 has an attachment component 50 which can be detachably attached to the needle mounting component 4b.

Because the injection needle 6 has the attachment component 50 which can be detachably attached to the needle mounting component 4b, the injection needle 6 can be mounted to the syringe cover 4. When this attachment component 50 is attached to the needle mounting component 4b, the lever 7 is pushed by the attachment component 50 and moves to the rear, and this movement is detected by the needle detector switch 8. Thus, the needle mounting state is detected.

(3-4)

The pharmaceutical injection device 101 in this embodiment further comprises the cap 3 and the cap detector switch 10 (an example of a cap detector). The cap 3 is detachably attached to the main case 2 so as to be disposed around the outer periphery of the pharmaceutical syringe 5 in a state of being mounted to the pharmaceutical syringe mounting component 1. The cap detector switch 10 detects the mounting state of the cap 3. If the mounting of the cap 3 has not been detected by the cap detector switch 10 after the first control (S19, S21), the controller 21 executes second control in which a message prompting the mounting of the cap 3 is displayed on the display component 19 (S23, S25).

Thus, the mounting state of the cap 3 during the switching off of the power switch 16 is checked, and if the cap 3 has not been mounted, a message to mount the cap 3 is displayed.

Consequently, the user can be prompted to mount the cap 3 and store the pharmaceutical injection device 101 in the storage case 29, which makes it less likely that the cap 3 will be lost.

(3-5)

The pharmaceutical injection device 101 in this embodiment comprises the charging terminal 20 and the charging detector 27 (an example of a charging detector). The charging terminal 20 is provided to the main case 2, and can be connected to the power supply terminal 31 provided on the outside. The charging detector 27 is connected via the charging circuit 25 to the charging terminal 20, and detects the charging state. If an uncharged state is detected in the charging circuit 25 by the charging detector 27 after second control, the controller 21 executes third control in which the display component 19 displays a message prompting the user to connect the charging terminal 20 to the power supply terminal 31 (S27, S29).

Thus, the connection state of the charging terminal 20 to the power supply terminal 31 in the switching off of the power switch 16 is detected, and if it is not a charged state, a message to perform charging is displayed.

Consequently, since the user can be prompted to store the pharmaceutical injection device 101 in the storage case 29 and perform charging and, it is less likely that the battery will be low when used the next time.

4. Other Embodiments (A)

In the above embodiment, the mounting of the injection needle 6 is directly detected using the needle detector switch 8 as an example of a needle detector, but this is not the only option.

As an example of indirectly detecting the mounting of the injection needle 6 to the pharmaceutical syringe 5, a color marker is provided at the distal end of the syringe cover 4, and when the injection needle 6 is mounted to the distal end of the syringe cover 4, this color marker is covered by the injection needle 6 and cannot be seen, so this mounting is indirectly detected.

In this case, a light emitting element and a light receiving element that are utilized in barcode readers and the like will be used.

(B)

In the above embodiment, the needle detector switch 8 is used as an example of a needle detector to directly detect the mounting of the injection needle 6 from its being pushed down by the lever 7, but a switch that is detected by being pushed down is not the only option. For example, an optical sensor having a light receiving element and a light emitting element may be provided, and movement of the lever 7 may be detected when the rear end 7c of the lever 7 blocks the light of the optical sensor.

(C)

In the above embodiment, the cap detector switch 10 is used as an example of a cap detector to detect the mounting of the cap 3 from its being pushed down by the lever 9, a switch is not the only option. For example, an optical sensor having a light receiving element and a light emitting element may be provided, and movement of the lever 7 may be detected when the rear end 9c of the lever 9 blocks the light of the optical sensor.

(D)

In the above embodiment, a display of "Attach needle" is given by the display component 19 as a direct message prompting the user to mount the injection needle 6, but this message may instead be indirect.

For example, the user may be indirectly prompted to mount the injection needle 6 by displaying a depiction of the injection needle 6 on the display component 19.

(E)

In the above embodiment, a display of "Remove needle" is given by the display component 19 as a direct message prompting the user to remove the injection needle 6, but this message may instead be indirect.

For example, the display component 19 may display a depiction of removing the injection needle 6 to indirectly prompt the user to remove the injection needle 6.

Embodiment 2

The pharmaceutical injection device 102 of Embodiment 2 will now be described through reference to FIGS. 8 to 14.

The pharmaceutical injection device 102 in Embodiment 2 has the same basic configuration as the pharmaceutical injection device 101 in Embodiment 1, but differs from Embodiment 1 in that the mounting of the injection needle 6 is detected indirectly. In Embodiment 2, those components that serve substantially the same function as in Embodiment 1 above will be numbered the same, but a 2 will be added to the hundreds place of the number when there is a significant change in the shape, etc.

1. Configuration 1-1. External Configuration of Pharmaceutical Injection Device 102

Figure 8:
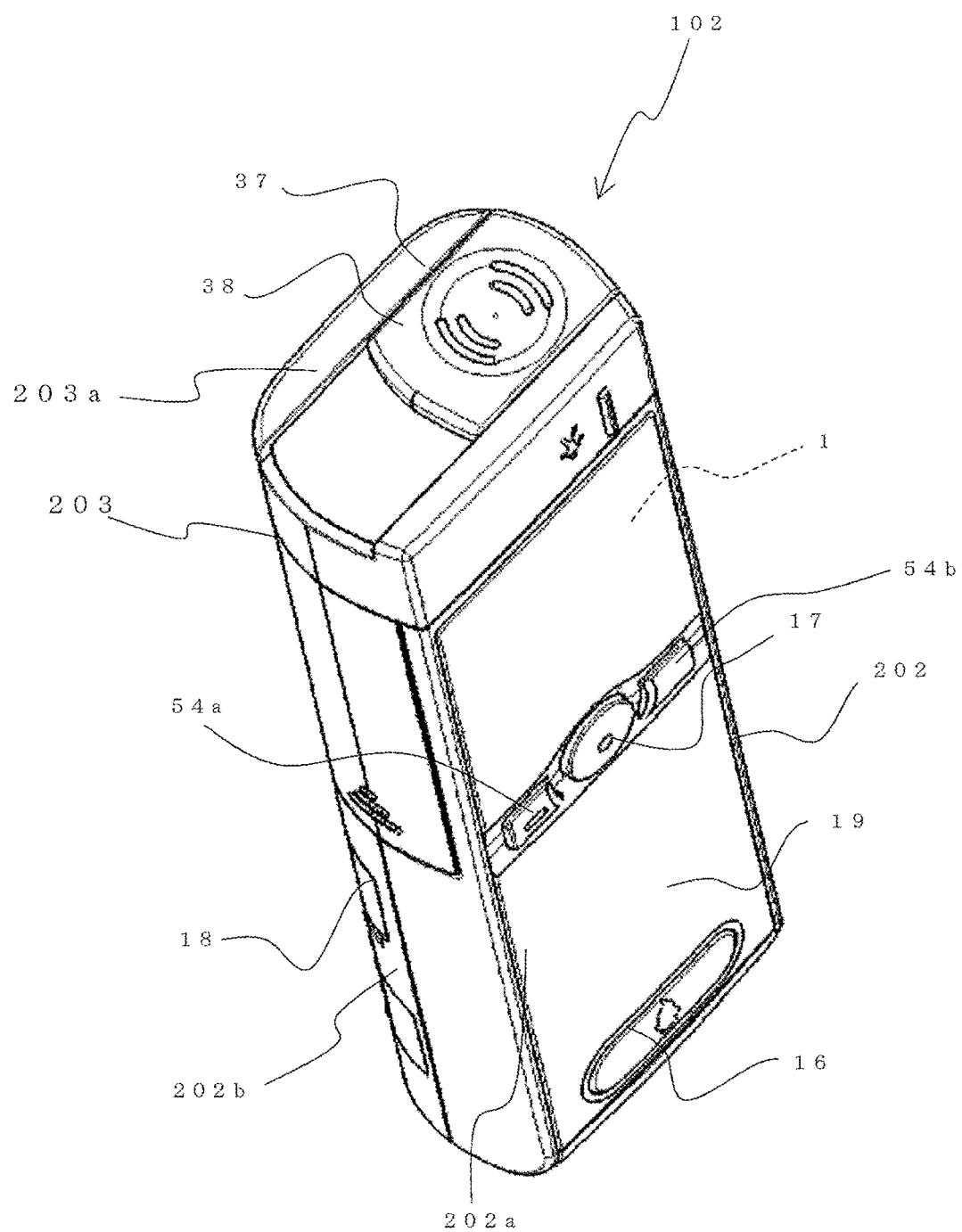
FIG. 8 is an oblique view of the pharmaceutical injection device in Embodiment 2 pertaining to the present invention.
Figure 9:
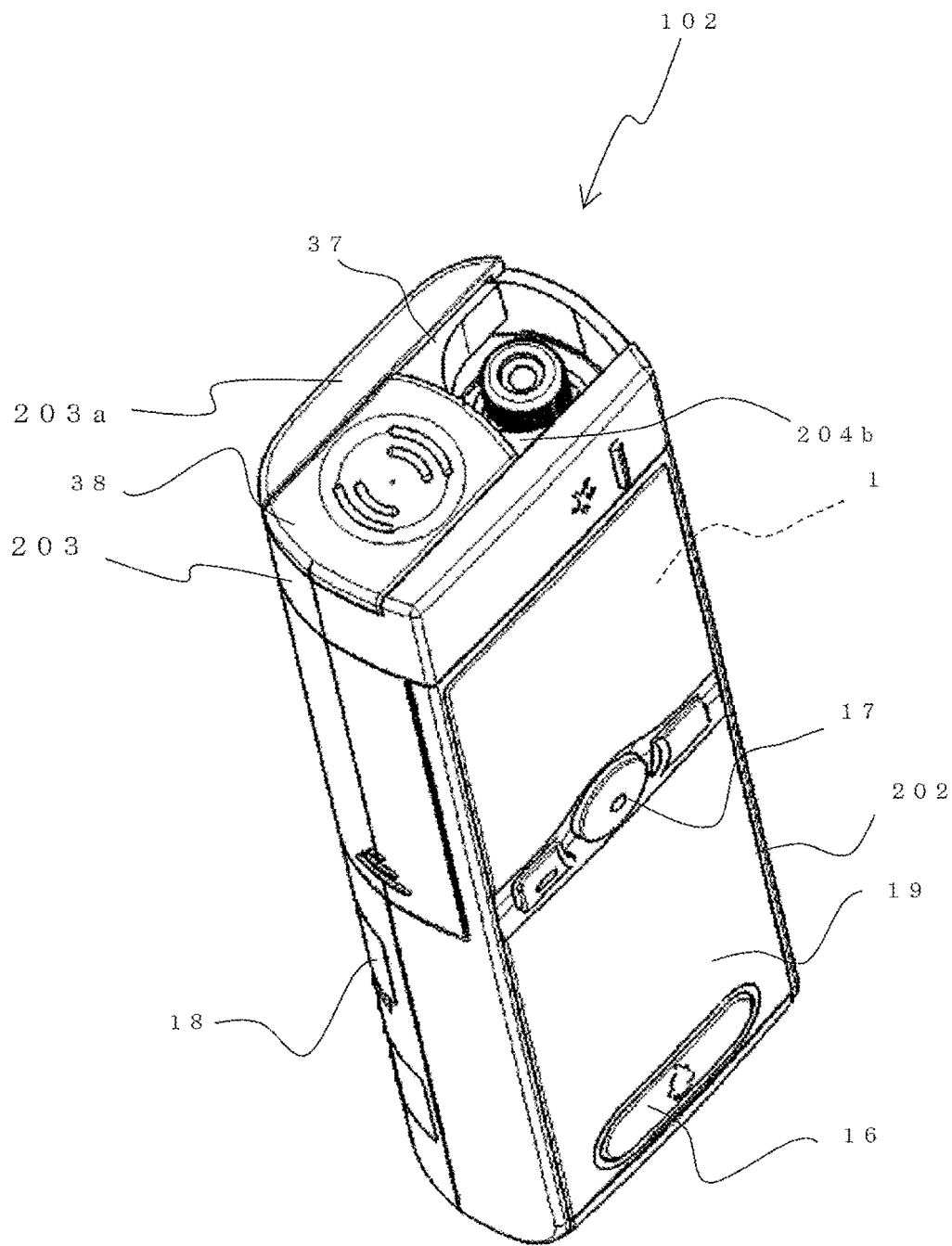
FIG. 9 is an oblique view of the state when the cover of the pharmaceutical injection device shown in FIG. 8 has been opened up.
Figure 10:
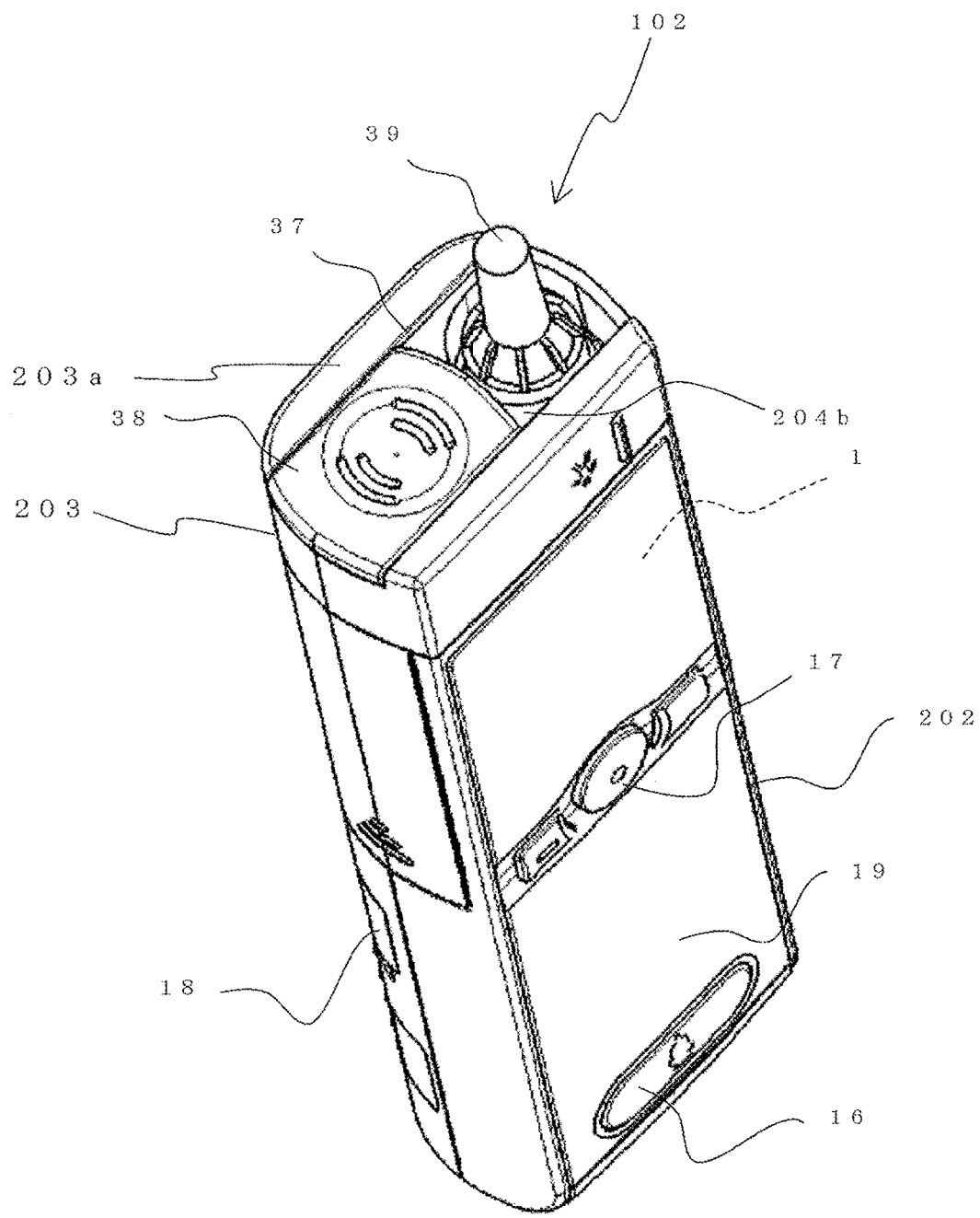
FIG. 10 is an oblique view of the state when the injection needle of the pharmaceutical injection device shown in FIG. 8 has been mounted along with a protective cap.
Figure 11:
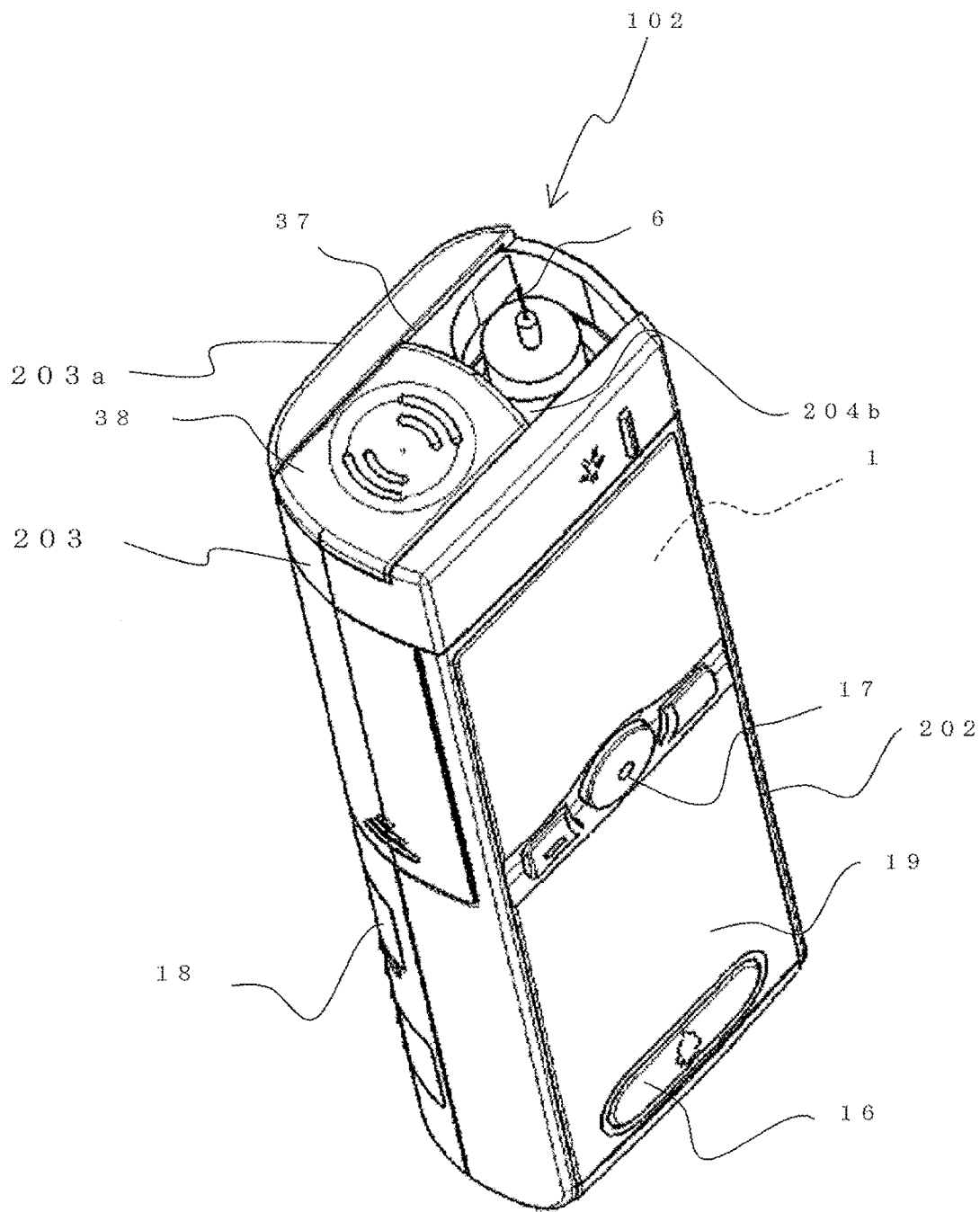
FIG. 11 is an oblique view of the state when the protective cap of the pharmaceutical injection device shown in FIG. 10 has been removed.

FIG. 8 is an oblique view of the pharmaceutical injection device 102 in Embodiment 2. FIG. 9 shows the state when the cover 38 of the pharmaceutical injection device 102 in the state shown in FIG. 8 has been opened up. In addition, FIG. 9 shows the state when a syringe cover 204 in which the pharmaceutical syringe 5 is housed is mounted to the pharmaceutical syringe mounting component 1. FIG. 10 is an oblique view of the state when the injection needle 6 has been mounted along with a cap 39 to the pharmaceutical injection device 102 in the state FIG. 9. FIG. 11 is an oblique view of the state when the cap 39 has been removed from the state of the pharmaceutical injection device 102 shown in FIG. 10.

As shown in FIG. 8, the pharmaceutical injection device 102 in Embodiment 2 comprises a substantially box-shaped main case 202 having the pharmaceutical syringe mounting component 1 on the inner distal end side. A cap 203 is detachably provided to this distal end side of the main case 202. An opening 37 is formed as shown in FIG. 9 in the face 203a on the distal end side of the cap 203. A cover 38 that is capable of sliding parallel to the face 203a is provided as shown in FIGS. 8 and 9 in order to open and close this opening 37. Thus, the cover 38 is provided to the cap 203 that is detachably mounted to the main case 202.

Also, if we let the side on which the cap 203 is disposed be the front side or the distal end side of the pharmaceutical injection device 102, and the opposite side thereof be the rear end side, the display component 19 is provided toward the rear end side of the front face 202a of the main case 202. The pharmaceutical injection switch 17 is disposed on the distal end side of the display component 19 on the front face 202a, and selector switches 54a and 54b are provided on both sides of the pharmaceutical injection switch 17 in the width direction. The power switch 16 is disposed at the end of the front face 202a on the rear end side.

In FIG. 8, the air vent switch 18 is provided to an end face 202b that is on the left side when viewed with the front face 202a at the front.

1-2. Internal Configuration of Pharmaceutical Injection Device 102

Figure 12:
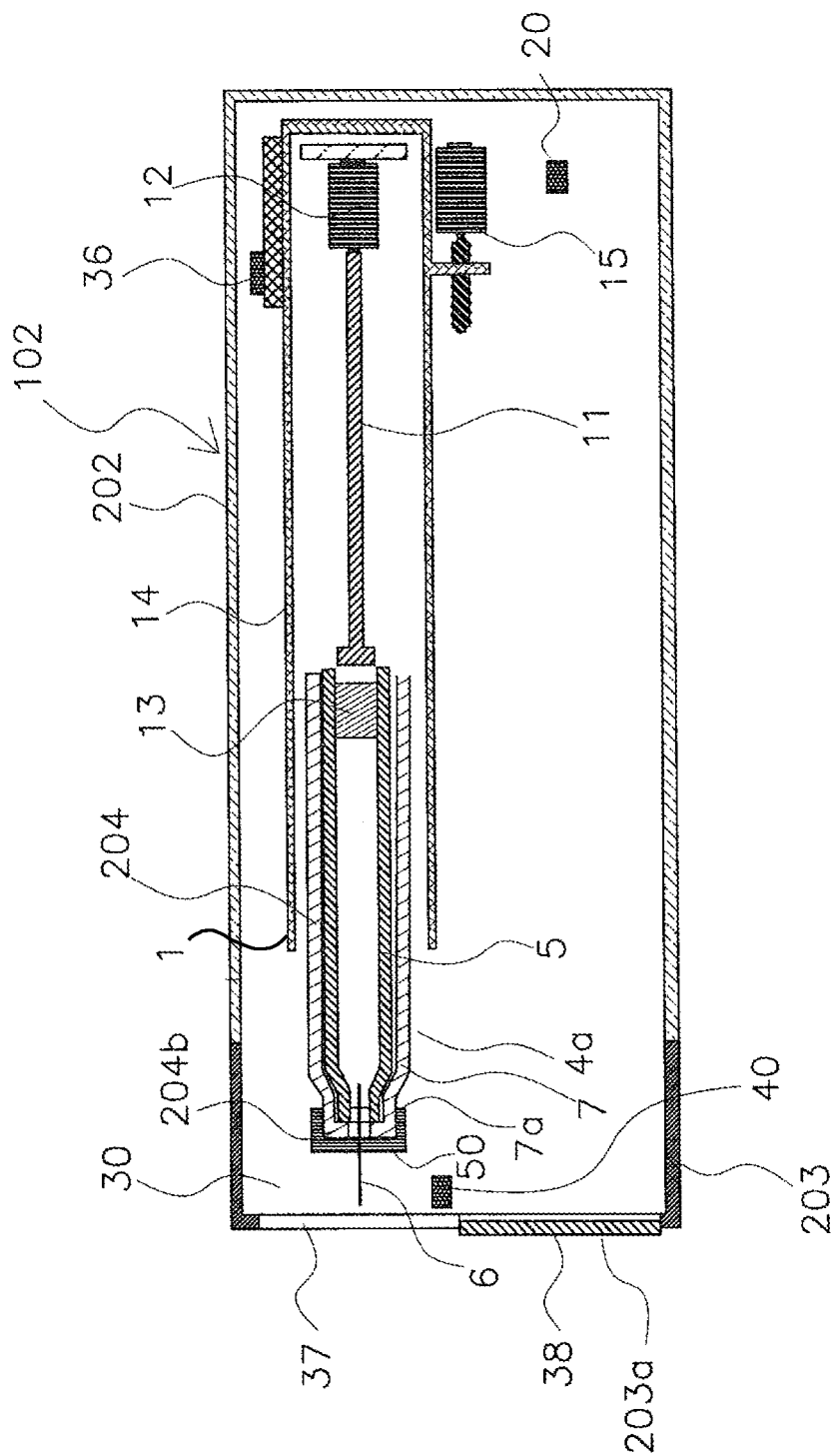
FIG. 12 is a simplified cross section of the pharmaceutical injection device shown in FIG. 8.

FIG. 12 is a simplified diagram of the internal configuration of the pharmaceutical injection device 102 in Embodiment 2.

As shown in FIG. 12, the pharmaceutical injection device 102 in Embodiment 2 is configured such that the syringe cover 204 is installed as shown in FIG. 9 in the pharmaceutical syringe mounting component 1. The syringe cover 204 in Embodiment 2 differs from the syringe cover 4 in Embodiment 1 in that the lever 7 is not provided. That is, the pharmaceutical injection device 102 in Embodiment 2 differs from Embodiment 1 in that the biasing component 51, the lever 7, and the needle detector switch 8 for directly detecting the mounting of the injection needle 6 are not provided.

Also, unlike in Embodiment 1, the biasing component 52, the lever 9, and the cap detector switch 10 for detecting the mounting of the cap 203 are not provided to the pharmaceutical injection device 102 in Embodiment 2.

Before the syringe cover 204 is mounted to the pharmaceutical syringe mounting component 1, the pharmaceutical syringe 5 is set inside the syringe cover 204 as shown in FIG. 12. Next, in a state in which the cap 203 has been detached from the main case 202, the syringe cover 204 in which the pharmaceutical syringe 5 is housed is mounted to the pharmaceutical syringe mounting component 1 from the distal end side.

The cap 203 is then mounted to the main case 202, and then the cover 38 of the opening 37 provided on the distal end side of the main case 202 is slid as shown in FIGS. 8 and 9 to open up the opening 37.

As shown in FIG. 9, in this state, the injection needle 6 is mounted along with the cap 39 to a needle mounting component 204b (see FIG. 10) on the distal end side of the syringe cover 204, resulting in a state in which the injection needle 6 is mounted to the pharmaceutical syringe 5.

As shown in FIG. 12, the piston 11 is provided just as in FIG. 2 in Embodiment 1, to the rear of the pharmaceutical syringe 5 inside the main case 202. The piston 11 is driven by the piston drive motor 12, which pushes the gasket 13 forward (distal end side) within the pharmaceutical syringe 5. This movement of the gasket 13 pushes the pharmaceutical out of the pharmaceutical syringe 5 through the injection needle 6.

Again in Embodiment 2, as shown in FIG. 12, just as in FIG. 2 in Embodiment 1, the moving member 14 is provided to house the piston 11, the piston drive motor 12, and the rear outer periphery of the syringe cover 204. This moving member 14 is configured so that it is driven forward and backward by the needle insertion and withdrawal drive motor 15.

In other words, again in this embodiment, just as in Embodiment 1, when the needle insertion and withdrawal drive motor 15 is first driven from the state in FIG. 12, the injection needle 6 moves forward together with the moving member 14. As a result, the injection needle 6 protrudes forward from the opening 37 of the main case 202, and this pierces the skin.

When the piston drive motor 12 is then driven, the gasket 13 is moved forward by the piston 11. As a result, the pharmaceutical in the pharmaceutical syringe 5 is injected into the human body through the injection needle 6.

In Embodiment 2, since the cap 3 of Embodiment 1 is not provided, the protective cap 39 is mounted as discussed above to the injection needle 6 (see FIG. 10). Removing the protective cap 39 from the injection needle 6 results in a state in which the injection needle 6 is exposed as shown in FIG. 11.

Therefore, the protective cap 39 is removed before the injection needle 6 is moved forward and pierces the skin, as shown in FIGS. 10 and 11. Then, the injection needle 6 is moved forward in the state in FIG. 11 and pierces the skin, and the pharmaceutical in the pharmaceutical syringe 5 is injected into the body from the injection needle 6.

In order to perform the above operation, the above-mentioned power switch 16, the pharmaceutical injection switch 17, the air vent switch 18, and the display component 19 are provided to the outer peripheral face of the main case 202 as discussed above. The charging terminal 20 is provided just as in Embodiment 1 to the outer peripheral face of the main case 202 of the pharmaceutical injection device 102 in Embodiment 2. This charging terminal 20 is the same as the one in FIG. 2, and is provided to the lower face side of the main case 202, SO it is not depicted in FIGS. 8 to 11, but is depicted in FIG. 12.

1-3. Control Configuration of Pharmaceutical Injection Device 102

Figure 13:
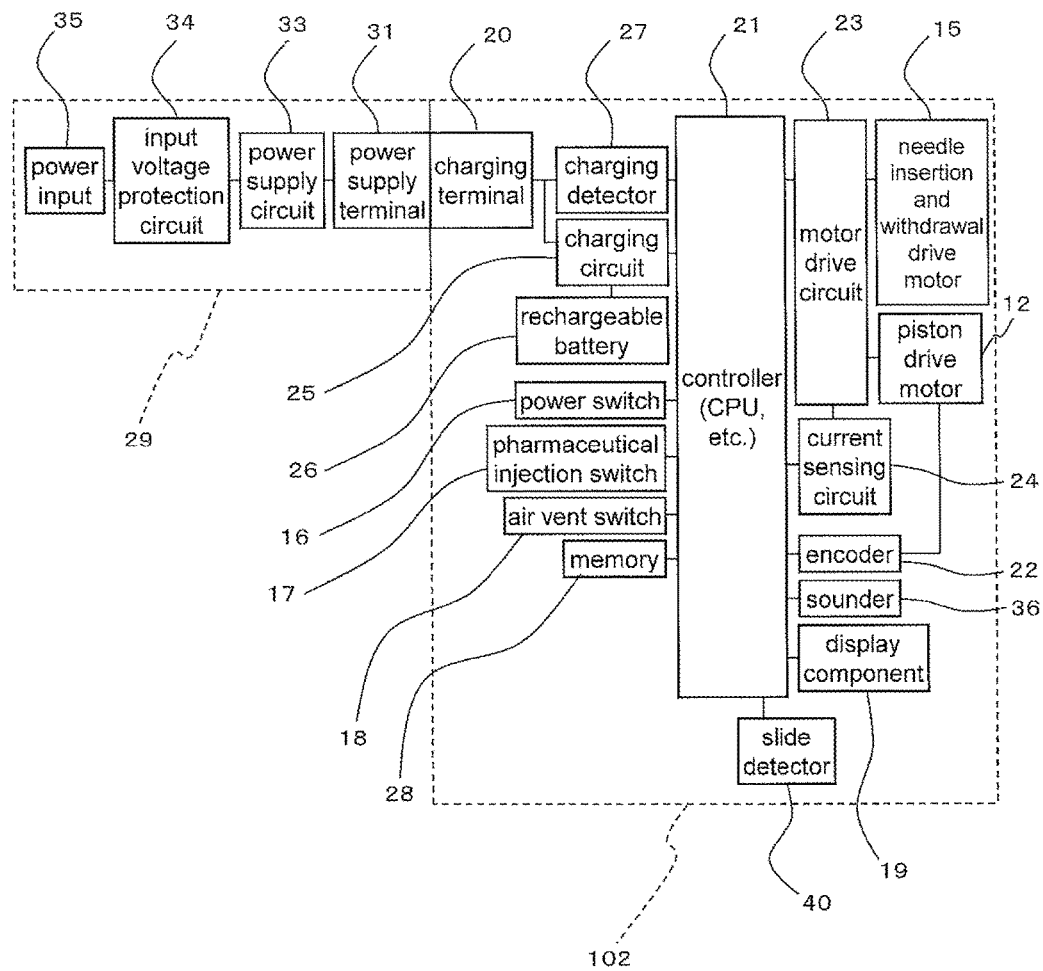
FIG. 13 is a control block diagram showing the simplified electrical configuration of the pharmaceutical injection device shown in FIG. 8 and its storage case.

FIG. 13 is a block diagram of the control configuration of the pharmaceutical injection device 102 in Embodiment 2.

The piston drive motor 12, the needle insertion and withdrawal drive motor 15, the power switch 16, the pharmaceutical injection switch 17, the air vent switch 18, the display component 19, and the charging terminal 20 are connected to the controller 21 as shown in FIG. 13.

Of these, the piston drive motor 12 is connected to the controller 21 via the encoder 22.

The piston drive motor 12 and the needle insertion and withdrawal drive motor 15 are connected to the controller 21 via the motor drive circuit 23.

The motor drive circuit 23 is connected to the controller 21 via the current sensing circuit 24.

The charging terminal 20 is connected to the rechargeable battery 26 via the charging circuit 25.

The charging terminal 20 is also connected to the controller 21 via the charging detector 27.

Similarly, the charging circuit 25 is also connected to the controller 21.

The memory 28, which stores control programs and the like, is connected to the controller 21.

Also, instead of the cap detector switch 10 used in Embodiment 1, the controller 21 is connected to a slide detector 40 for whether the cover 38 is open or closed.

1-4. Slide Detector 40

Figure 14:
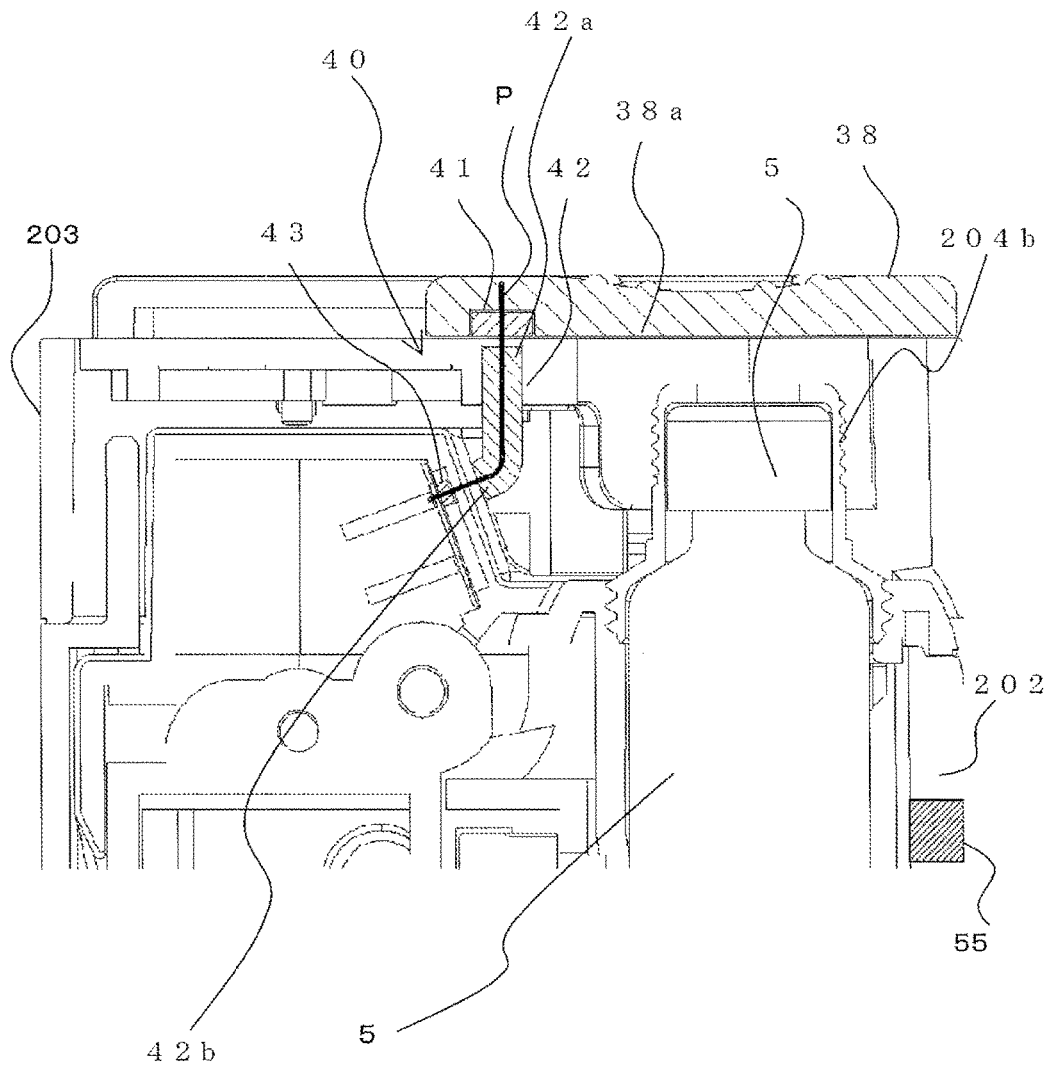
FIG. 14 is a detail cross section of the pharmaceutical injection device shown in FIG. 8.

FIG. 14 is a cross section of the configuration near of the slide detector 40. As shown in FIG. 14, the slide detector 40 comprises a magnet 41, a yoke 42, and a magnetic sensor 43. The magnet 41 is provided on the back face 38a of the cover 38, and is magnetized in a direction substantially perpendicular to the slide direction of the cover 38 (this could also be said to be a direction substantially perpendicular to the back face 38a).

The yoke 42 is made of a soft magnetic material such as silicon steel or electromagnetic soft iron. The term "soft magnetic material" means a magnetic material whose magnetic permeability is high and whose coercivity is low. The yoke 42 is disposed such that one end 42a on the distal end side is opposite the magnet 41 in a state in which the cover 38 is closed (a state in which the opening 37 is covered by the cover 38), and the other end 42b on the rear end side is opposite the magnetic sensor 43. With this arrangement, the yoke 42 guides the magnetic flux generated by the magnet 41 when cover 38 is closed to the magnetic sensor 43, as indicated by the arrow P in the drawings.

The magnetic sensor 43 is connected to the controller 21 shown in FIG. 13, and outputs a signal to the controller 21 when a magnetic field is detected.

Specifically, as shown in FIG. 14, in the closed state of the cover 38, since one end of the yoke 42 is opposite the magnet 41, most of the magnetic flux from the magnet 41 flows to the magnetic sensor 43 that is disposed opposite the other end of the yoke 42, and as a result, the magnetic sensor 43 can detect that the cover 38 is closed.

The controller 21 detects that the output of the magnetic sensor 43 is in its on state, and determines that the cap 203 has been mounted to the main case 202, and that the cover 38 is closed.

1-5. Storage Case

The pharmaceutical injection device 102 in Embodiment 2 configured as above is similar to Embodiment 1 in that it is stored in the storage case 29 as shown in FIGS. 4 and 5, and the rechargeable battery 26 is charged during this storage. The storage case in Embodiment 2 differs only in the shape of the mounting recess 30, but its function is the same as that in Embodiment 1, so it will be described by referring to the storage case 29 of FIGS. 4 and 5.

More specifically, as shown in FIG. 4, the storage case 29 has the lid 32 and the placement component 53 in which is formed the mounting recess 30 in which the main case 202 of the pharmaceutical injection device 102 is mounted. The mounting recess 30 is formed to conform to the exterior shape of the pharmaceutical injection device 102 in a state in which the cap 203 has been mounted to the main case 202. When the main case 202 to which the cap 203 has been mounted is mounted in the mounting recess 30, just as in FIG. 6, the power supply terminal 31 provided to the mounting recess 30 comes into contact with the charging terminal 20 of the main case 202, and the rechargeable battery 26 is charged.

Again in Embodiment 2, in order to put the pharmaceutical injection device 102 in the storage case 29 for charging, the lid 32 in the state in FIG. 5 is configured to be closed and mate with the placement component 53 so as to cover the mounting recess 30 and the pharmaceutical injection device 102.

Also, the power supply terminal 31 is connected to the power input 35 via the power supply circuit 33 and the input voltage protection circuit 34, just as in FIG. 3. This power input 35 has a plug or the like that allows it to be plugged into an outlet, etc.

2. Operation

Figure 15A:
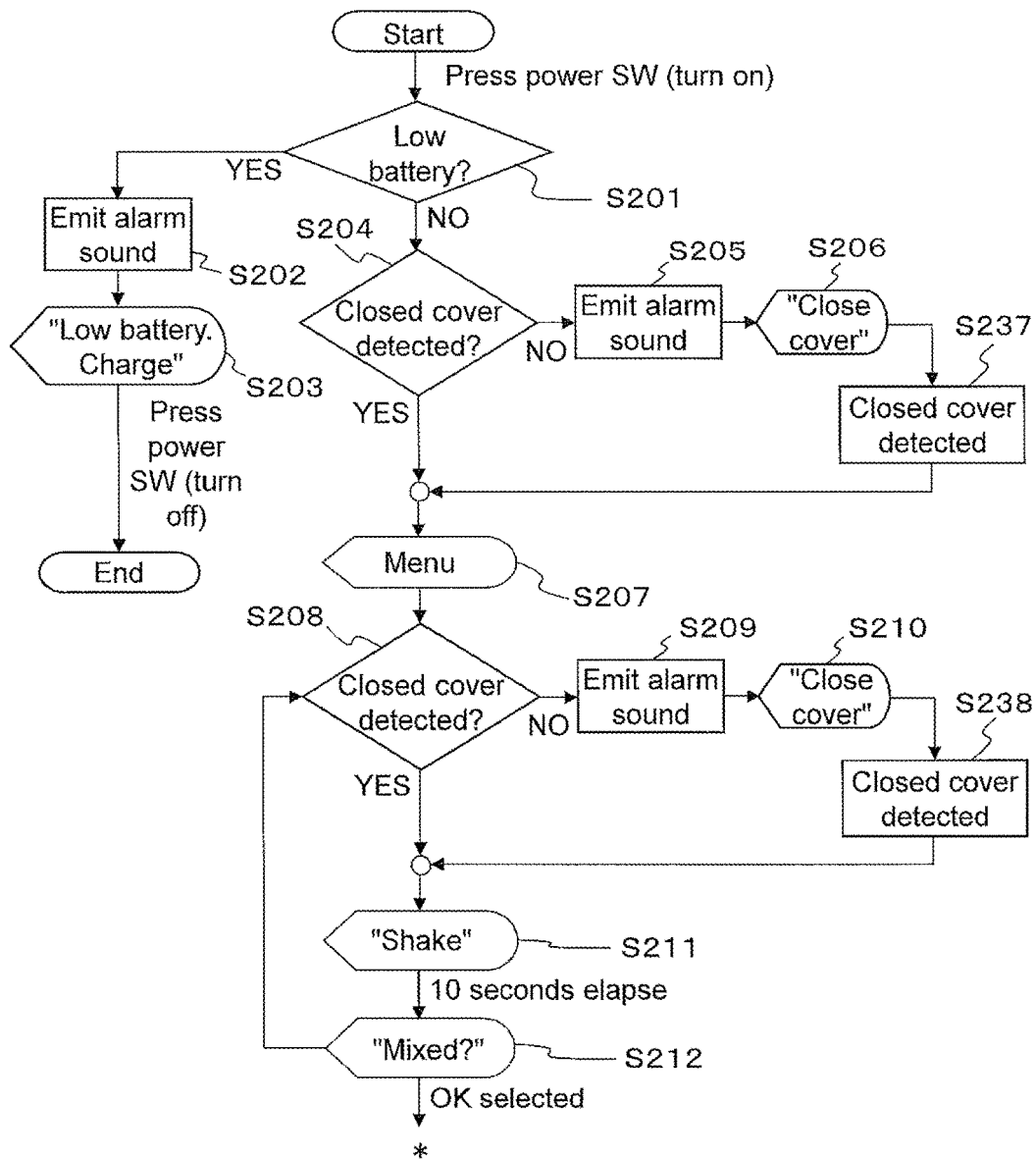
FIG. 15A is a flowchart of the operational control of the pharmaceutical injection device shown in FIG. 8.
Figure 15B:
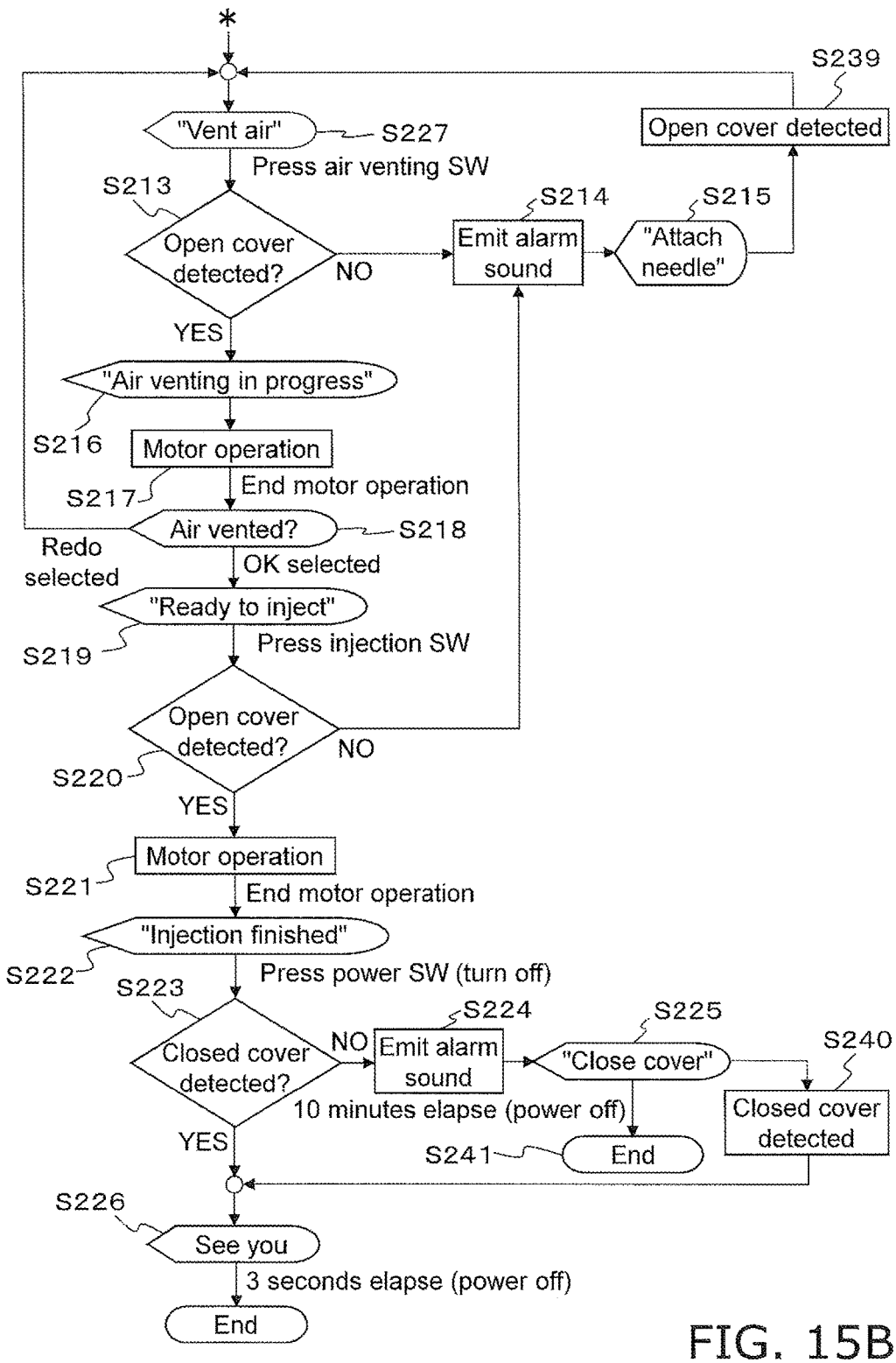
FIG. 15B is a flowchart of the operational control of the pharmaceutical injection device shown in FIG. 8.

FIGS. 15A and 15B are flowcharts of the operation of the pharmaceutical injection device 102 in Embodiment 2.

In the above configuration, when injecting the pharmaceutical, the pharmaceutical injection device 102 is as shown in FIG. 9, in which the syringe cover 204 that houses the pharmaceutical syringe 5 is mounted to the pharmaceutical syringe mounting component 1 of the main case 202, and the injection needle 6 covered by the protective cap 39 is mounted to the syringe cover 204.

Next, the protective cap 39 is pulled off as shown in FIG. 11 to expose the injection needle 6.

When the injection needle 6 covered by the protective cap 39 is mounted to the syringe cover 204, or when the protective cap 39 is pulled off to expose the injection needle 6, the cover 38 is slid to open up the opening 37, with the mounting and removal being performed through this opening 37.

In this state, first the power switch 16 (labeled as power supply SW in FIGS. 15A and 15B) pushed down and put in its on state.

The controller 21 then senses the voltage of the rechargeable battery 26 via the charging circuit 25 (S201 in FIG. 15A).

Then, if the voltage of the rechargeable battery 26 is low, the controller 21 emits an alarm sound from the sounder 36 connected to the controller 21 as shown in FIG. 13 (S202 in FIG. 15A), and then a message prompting the user to charge the battery is displayed on the display component 19 (S203 of FIG. 15A). More specifically, the display component 19 displays a message of "Low battery; charge." After the message is displayed, the power switch 16 is pressed by the user, the power supply is switched off, and control is ended.

When the voltage of the rechargeable battery 26 is at the proper level, first the slide detector 40 indirectly detects whether or not the injection needle 6 has been mounted to the pharmaceutical syringe 5 (S204 in FIG. 15A).

That is, in Embodiment 1 the fact that the injection needle 6 had been mounted to the pharmaceutical syringe 5 is directly detected by the needle detector switch 8, but in Embodiment 2 whether or not the injection needle 6 has been mounted to the pharmaceutical syringe 5 is detected indirectly by slide detector 40.

More precisely, in a state in which the cover 38 has been slid to open up the opening 37, the injection needle 6 is in a state of being mounted to the pharmaceutical syringe 5, so at this point the controller 21 indirectly determines that the injection needle 6 has been mounted to the pharmaceutical syringe 5.

Also, even when the moving member 14 is positioned all the way to the rear end side, the injection needle 6 is long enough to protrude beyond the opening 37. Therefore, in a state in which the injection needle 6 has been mounted to the pharmaceutical syringe 5, the cover 38 cannot be slid to close off the opening 37 because the injection needle 6 is in the way.

For this reason, in Embodiment 2, whether or not the injection needle 6 has been mounted to the pharmaceutical syringe 5 is detected indirectly by the slide detector 40 (S204 in FIG. 15A).

It is determined that the injection needle 6 has been mounted, the controller 21 emits an alarm sound from the sounder 36 (S205 in FIG. 15A), then causes the display component 19 to display a message prompting the user to remove the injection needle 6 (S206 in FIG. 15A). More specifically, the controller 21 causes the display component 19 to display a direct indication of "Close cover." This display consequently (indirectly) instructs the user to remove the injection needle 6.

In S204 in FIG. 15A, if the cover 38 is determined to be closed, the controller 21 causes the display component 19 to display a menu (S207 in FIG. 15A). The control also proceeds to S207 if it is detected that the cover 38 is closed (S237) after the display in S206.

Figure 16A:
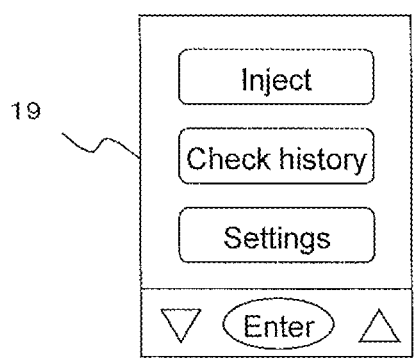
FIGS. 16*a* to 16*c* show display examples of the display component of the pharmaceutical injection device shown in FIG. 8.

More specifically, in S207, the display shown in FIG. 16a is given. In FIG. 16a, "Inject," "Check history," and "Settings" are displayed as menus. An "Enter" key is displayed under these, and up and down arrow keys are displayed on the left and right of the display of the "Enter" key. The selector switches 54a and 54b are disposed under the up and down arrow keys, "Inject," "Check history," and "Settings" can be selected by pressing these selector switches 54a and 54b, and this action can be entered by pressing the pharmaceutical injection switch 17 disposed under the "Enter" key.

Here, when the inject is selected, the controller 21 checks the open or closed state of the cover 38 again (S208 in FIG. 15A).

More specifically, if the cover 38 is not closed, the controller 21 emits an alarm sound from the sounder 36 (S209 in FIG. 15A), then displays on the display component 19 a message prompting the user to remove the injection needle 6 (S210 in FIG. 15A). The controller 21 gives an indirect display of "Close cover" on the display component 19. This display indirectly tells the user to remove the injection needle 6.

In S208 of FIG. 15A, if the cover 38 is determined to be closed, the controller 21 displays "Shake" on the display component 19 (S211 in FIG. 15A). The control also proceeds to S211 when it is detected that the cover 38 is closed after the display in S210.

That is, better uniformity can be attained by stirring the pharmaceutical in the pharmaceutical syringe 5 mounted in the main case 202.

Figure 16B:
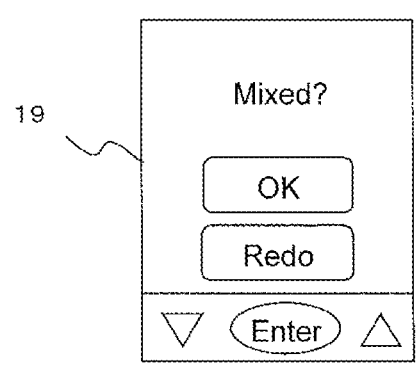

Then, after 10 seconds has elapsed, the controller 21 displays "Mixed?" on the display component 19. Here, specifically, in S212, the display shown in FIG. 16b is given. In FIG. 16b, along with the display of "Mixed?," menus of "OK" and "Redo" are displayed. Also, an "Enter" key is displayed below these displays, and up and down arrow keys are displayed on the left and right of the display of the "Enter" key. Either "OK" or "Redo" can be selected by using the pharmaceutical injection switch 17 and the selector switches 54a and 54b just as discussed above. In addition, a check window 55 (see FIG. 14), for example, is provided so that the user can check the state in the pharmaceutical syringe 5, and the user can look through the check window 55 to determine whether or not the pharmaceutical is mixed.

In S212, when the "OK" key displayed simultaneously with the display of "Mixed?" is operated pressed, the controller 21 causes the display component 19 to give a display prompting the user to vent the air (S227 in FIG. 15B). On the other hand, if "Redo" is selected, the control returns to S208, and "Shake" is displayed again.

At this point, if the air vent switch 18 shown in FIG. 11 is pressed, the controller 21 uses the slide detector 40 to detect whether or not the cover 38 is open (S213 in FIG. 15B).

That is, to vent the air, it is important that the injection needle 6 is mounted to the pharmaceutical syringe 5, and the mounting of the injection needle 6 to the pharmaceutical syringe 5 is detected indirectly from whether the cover 38 is open or closed.

Therefore, if the cover 38 is closed, the controller 21 emits an alarm sound from the sounder 36 (S214 in FIG. 15B), then displays on the display component 19 a message prompting the user to mount the injection needle 6 (S215 in FIG. 15B). The display at this point is a direct display of "Attach needle," but the display component 19 may instead display an image of the injection needle 6 as an indirect display. After the message of "Attach needle" is displayed in S215, if the slide detector 40 has detected that the cover 38 is open (S239), control returns to S227, and a message of "Vent air" is displayed again.

Then, if the mounting of the injection needle 6 to the pharmaceutical syringe 5 is indirectly detected in S213 in FIG. 15B from the fact that the cover 38 has been opened, the controller 21 causes the display component 19 to display "Air venting in progress" (S216 in FIG. 15B). Following this display, the needle insertion and withdrawal drive motor 15 is then driven. Next, the piston drive motor 12 is driven to execute the air venting.

Then, when the air venting is complete, the needle insertion and withdrawal drive motor 15 is reversed, and the injection needle 6 returns to the state in FIG. 11 (S217 in FIG. 15B).

In Embodiment 2, the needle was inserted and withdrawn using the needle insertion and withdrawal drive motor 15, but even when the needle has been removed, the injection needle 6 protrudes beyond the opening 37 of the main case 202, as shown in FIG. 10.

If the injection needle 6 is thus long enough to protrude from the opening 37, the piercing operation can be performed manually by the patient, a healthcare worker, or the like by holding the main case 202, so if the main case 202 is made more compact, the needle insertion and withdrawal drive motor 15 can be eliminated.

In any case, in Embodiment 2, since the injection needle 6 protrudes from the opening 37 of the main case 202 in a state in which the injection needle 6 has been mounted to the pharmaceutical syringe 5 and the cover can not be closed, the slide detector 40 can detected that the cover 38 is closed, or that the cover 38 is open. Thus, even when the needle has been withdrawn, the injection needle 6 protrudes outward beyond the opening 37, so when it is detected that the cover 38 is closed, the injection needle 6 can be determined not to have been mounted. That is, the mounting state of the injection needle 6 can be indirectly detected from whether the cover 38 is open or closed.

Figure 16C:
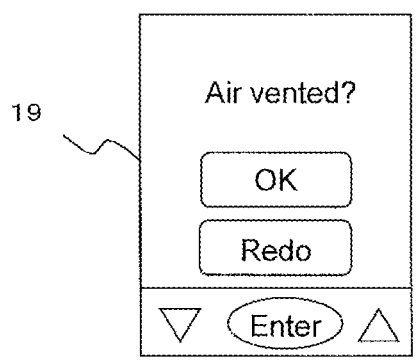

When this air venting is complete, the controller 21 causes the display component 19 to display "Air vented?" (S218 in FIG. 15B). More specifically, in S218, the display shown in FIG. 16c is given. In FIG. 16c, menus of "OK" and "Redo" are displayed along with the display of the "Air vented?" Also, an "Enter" key is displayed below these displays, and up and down arrow keys are displayed on the left and right of the display of the "Enter" key. Either "OK" or "Redo" can be selected by using the pharmaceutical injection switch 17 and the selector switches 54a and 54b just as discussed above. In addition, the user can visually confirm that pharmaceutical is coming out of the distal end of the injection needle 6, and can thereby determine whether or not the air has been vented.

At this point, when the OK key displayed on the display component 19 is pressed, the controller 21 causes the display component 19 to display "Ready to inject" (S219 in FIG. 15B). On the other hand, if the "Redo" key is pressed, control returns to S227 and the air venting operation is performed again.

When "Ready to inject" is displayed in S219, if the user places the opening 37 of the main case 202 against the pharmaceutical administration site (the skin), the injection needle 6 pierces the skin. The pharmaceutical injection switch 17 is then operated by the user.

Then, the controller 21 again checks whether the cover 38 is open or closed (S220 in FIG. 15B).

If the cover 38 is closed, the controller 21 issues an alarm sound from the sounder 36 (S214 in FIG. 15B), then causes the display component 19 to display a message prompting the user to mount the injection needle 6 (S215 in FIG. 15B).

In other words, it can be concluded that the injection needle 6 has not been mounted to the pharmaceutical syringe 5 from the fact that the cover 38 is closed, even though the pharmaceutical injection switch 17 has been operated in an attempt to perform pharmaceutical injection, so an alarm sound is emitted from the sounder 36 (S214 in FIG. 15B), and then a message prompting the user to mount the injection needle 6 is displayed on the display component 19 (S215 in FIG. 15B). If the slide detector 40 has detected that the cover 38 was opened after a message to "Attach needle" was displayed in S215 (S239), control returns to S227, and a message to "Vent air" is displayed again.

In contrast, if the cover 38 is opened in S220 in FIG. 15B, this is a state in which it is indirectly determined that the injection needle 6 has been mounted to the pharmaceutical syringe 5, so at this point, first the needle insertion and withdrawal drive motor 15 is operated, resulting in a state in which the injection needle 6 further pierces the pharmaceutical administration site through the opening 37 in the main case 202. Next, the piston drive motor 12 causes the piston 11 to push the gasket 13, the result of which is that the pharmaceutical in the pharmaceutical syringe 5 is injected into the body through the injection needle 6 (S221 in FIG. 15B).

Once this pharmaceutical injection is complete, the piston drive motor 12 and the needle insertion and withdrawal drive motor 15 are reversed. As a result, the injection needle 6 goes back toward the inside of the main case 202, and the piston 11 is also withdrawn from the pharmaceutical syringe 5.

Then, the controller 21 is informs the user that the pharmaceutical injection is complete by displaying "Injection finished" on the display component 19 (S222 in FIG. 15B).

When the power switch 16 is turned off in this state, the controller 21 confirms that the cover 38 is closed (S223 in FIG. 15B).

That is, the purpose of this step S223 is to determine whether or not the cover 38 has been closed after completion of the injection of the pharmaceutical. More specifically, when the pharmaceutical injection is complete, the user removes the injection needle 6 from the pharmaceutical syringe 5 and closes the cover 38 to store the pharmaceutical syringe 5 inside the main case 202.

Therefore, in S223, it can be determined that the injection needle 6 is still attached to the pharmaceutical syringe 5 by the cover 38 being not closed, so at this point an alarm sound is emitted from the sounder 36 (S224 in FIG. 15B). The controller 21 then causes the display component 19 to display the message "Close cover" (S225 in FIG. 15B). Thus, the user is indirectly prompted to remove the injection needle 6 by displaying "Close cover."

Also, in S223, if the slide detector 40 has detected that the cover 38 is closed, the controller 21 determines that the injection needle 6 has been properly removed from the pharmaceutical syringe 5, and therefore causes the display component 19 to display the message "See you" to end the operation (S226 in FIG. 15B).

In S225, if the slide detector 40 detects that the cover 38 is closed after displaying the message "Close cover" (S240), control proceeds to S226 and the message of "See you" is displayed.

Also, if it is not detected that the cover 38 is closed even after 10 minutes have elapsed since the display in S225, the power shut off and control is ended in order to reduce power consumption (S241).

3. Key Features (3-1)

The pharmaceutical injection device 102 in Embodiment 2 comprises the main case 202, the piston 11, the piston drive motor 12 (an example of a driver), the power switch 16, the display component 19, and the controller 21. The main case 202 has the pharmaceutical syringe mounting component 1 to which the pharmaceutical syringe 5 is mounted. The piston 11 is provided movably with respect to the pharmaceutical syringe 5 mounted to the pharmaceutical syringe mounting component 1. The piston drive motor 12 drives the piston 11. The power switch 16 switches the power on and off. The display component 19 is provided to the main case 202. The slide detector 40 (an example of a needle detector) indirectly detects the mounting state of the injection needle 6. When the slide detector 40 indirectly detects that the injection needle 6 has been mounted in the switching off of the power switch 16, a first control is executed to cause the display component 19 to display a message that indirectly prompts the user to remove the injection needle 6 (S223, S225).

Thus, when the mounting state of the injection needle 6 is indirectly checked in the switching off of the power switch 16 and it is detected that the injection needle 6 has been mounted, a message prompting the user to remove the injection needle 6 is displayed.

Consequently, the user can be prompted to remove the injection needle 6 and put away the pharmaceutical injection device 102 in the storage case 29, so the user will be less likely to forget to remove the injection needle 6 when the device is put away.

Therefore, the user will also be less likely to reuse an injection needle 6 that has already been used.

(3-2)

The pharmaceutical injection device 102 in Embodiment 2 further comprises the cap 203. The cap 203 is disposed on the distal end side of the pharmaceutical syringe mounting component 1, and is detachably attached to the main case 202. The cap 203 has the opening 37 formed opposite the distal end of the pharmaceutical syringe mounting component 1, and the cover 38 for opening and closing the opening 37. The injection needle 6 protrudes from the opening 37 in its mounted state. The slide detector 40 (an example of a needle detector) indirectly detects the mounting state of the injection needle 6 by detecting whether the cover 38 is open or closed.

In a state in which the injection needle 6 is mounted, the cover 38 cannot be closed since the injection needle 6 protrudes from the opening 37. Therefore, in a state in which the cover 38 is closed, can be concluded that the injection needle 6 has not been mounted.

Consequently, the fact that the injection needle 6 has not been mounted can be indirectly detected by detecting whether the cover 38 is open or closed, and the user will be less likely to forget to remove the injection needle 6.

(3-3)

The pharmaceutical injection device 102 in Embodiment 2 is such that the slide detector 40 has the magnet 41, the yoke 42, and the magnetic sensor 43. The magnet 41 is provided to the cover 38. The yoke 42 is disposed inside the main case 202 so as to be opposite the magnet 41 in a state in which the cover 38 is closed. The magnetic sensor 43 is disposed opposite the yoke 42.

Consequently, the when cover 38 is closed, the magnetic flux generated by the magnet 41 is guided by the yoke 42 to the magnetic sensor 43, and the magnetic sensor 43 detects this magnetism. This makes it possible to detect that the cover 38 is closed.

4. Other Embodiments (A)

In Embodiment 2, in S223 and S225, control is ended after it is indirectly detected that injection needle 6 have been removed, but third control of detecting the charging state shown in S27, S28, and S29 in Embodiment 1 may be performed after the cover detection in S223.

In Embodiment 2, since the cover 38 is provided to the cap 203, the mounting of the cap 203 is detected along with the removal of the injection needle 6 by detecting that the cover 38 is closed. Therefore, it is not necessary to provide the second control shown in S23 and S25 in Embodiment 1. In other words, the second control shown in S23 and S25 in Embodiment 1 is already included in the first control shown in S223 and S225 in Embodiment 2.

(B)

In Embodiment 2, in S225 the user is indirectly prompted to remove the injection needle by displaying a message of "Close cover," but may instead be directly prompted to remove the injection needle with a message of "Remove needle."

(C)

The message of "Close cover" may indicate the closing of the cover not only directly, but also indirectly.

The indirect display for closing the cover 38 may also be a display of an image of closing the cover on the display component 19.

Embodiment 3

Next, the pharmaceutical injection device 103 in a third embodiment of the present invention will be described through reference to FIGS. 17 to 23. In Embodiment 3, components that perform the same function as in the Embodiments 1 and 2 will be numbered the same, but a 3 will be added in the hundreds place of the number when there is a significant change in the shape, etc.

In Embodiment 3, the needle insertion and withdrawal drive motor 15 used in Embodiments 1 and 2 is not provided, and needle insertion and withdrawal are performed by the patient, a healthcare worker, etc.

In other words, with the pharmaceutical injection device 101 in Embodiment 1, since the injection needle 6 is to the rear of the cap 3, the injection needle 6 is moved forward by the needle insertion and withdrawal drive motor 15 until it protrudes from the cap 3 and pierces the skin. After this, the injection needle 6 is moved backward by the needle insertion and withdrawal drive motor 15 to withdraw the needle.

Also, in Embodiment 2, as can be understood from FIG. 11, in a state in which the injection needle 6 is mounted to the pharmaceutical syringe 5, the distal end of the injection needle 6 protrudes slightly in front of the main case 202 through the opening 37.

Accordingly, when piercing the skin, the patient, healthcare worker, or the like lightly places the injection needle 6 on the injection site, and then the injection needle 6 is moved forward by the needle insertion and withdrawal drive motor 15, and the needle is inserted to the proper depth. Then, after the pharmaceutical injection, the injection needle 6 is refracted by needle insertion and withdrawal drive motor 15, and finally the injection needle 6 is withdrawn by the patient, healthcare worker, etc.

In Embodiment 3, the distance by which the injection needle 6 protrudes from the opening 37 is longer than in Embodiment 2.

That is, the user holds the main case 202 and positions the injection needle 6 opposite the injection site, and then pushes until the site hits the cover 38, whereupon the injection needle 6 is inserted to the proper depth into the body.

Specifically, the pharmaceutical injection device 103 in Embodiment 3 is configured such that the insertion and withdrawal of the injection needle 6 are performed without using the needle insertion and withdrawal drive motor 15, and eliminating the needle insertion and withdrawal drive motor 15 allows the main case 202 to be made more compact.

Figure 17:
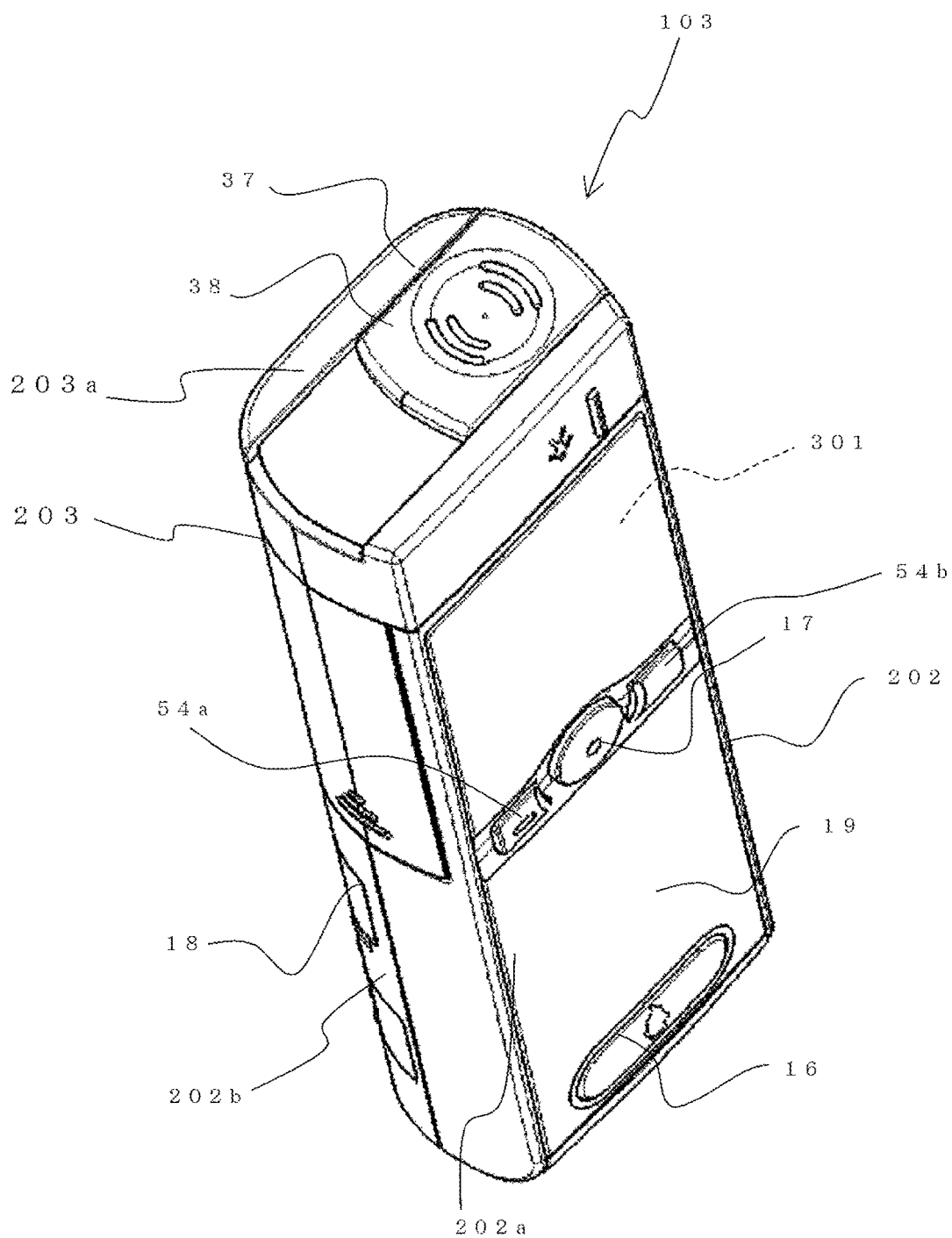
FIG. 17 is an oblique view of the pharmaceutical injection device in Embodiment 3 pertaining to the present invention.
Figure 18:
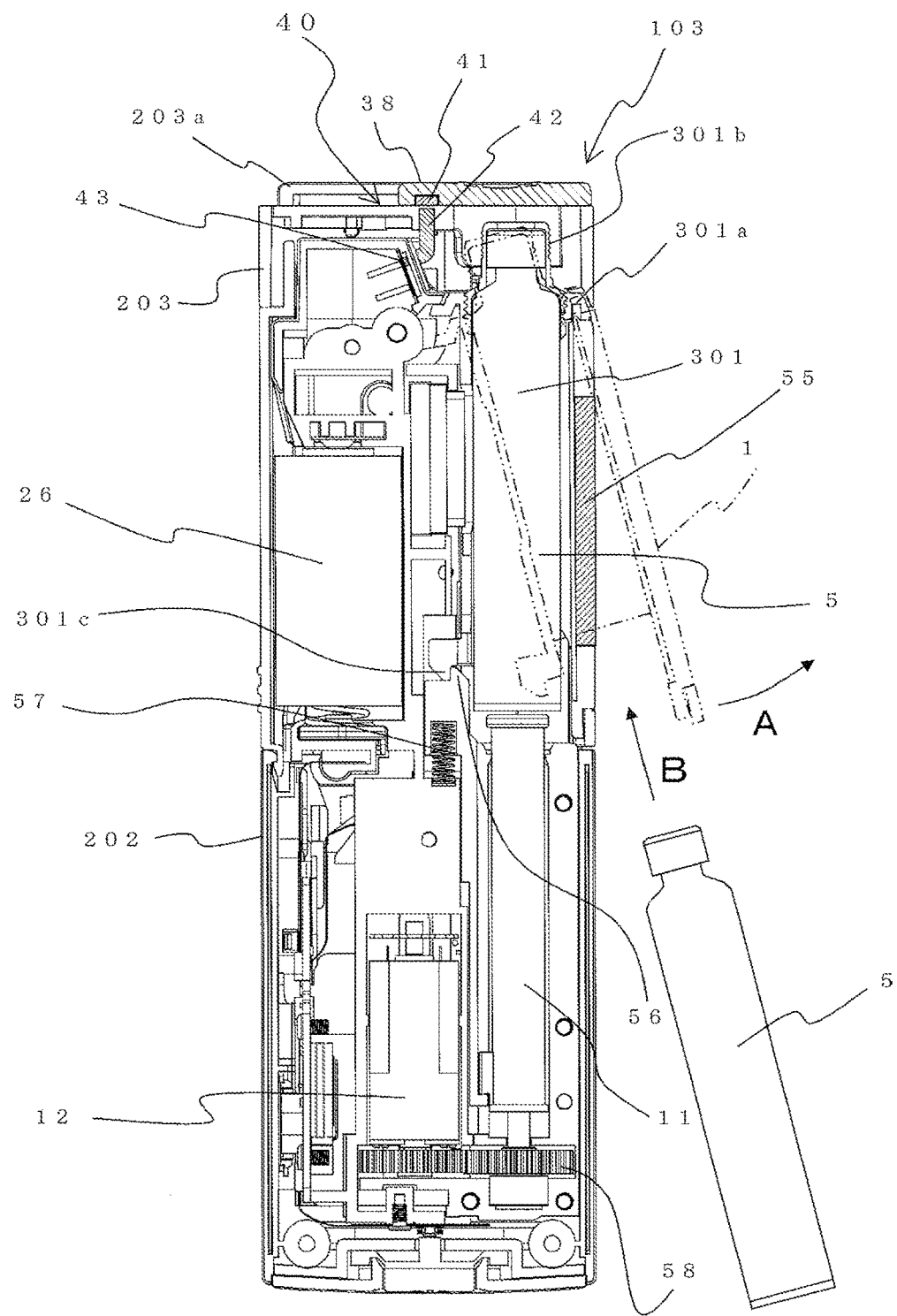
FIG. 18 is a cross section of the pharmaceutical injection device shown in FIG. 17.
Figure 19:
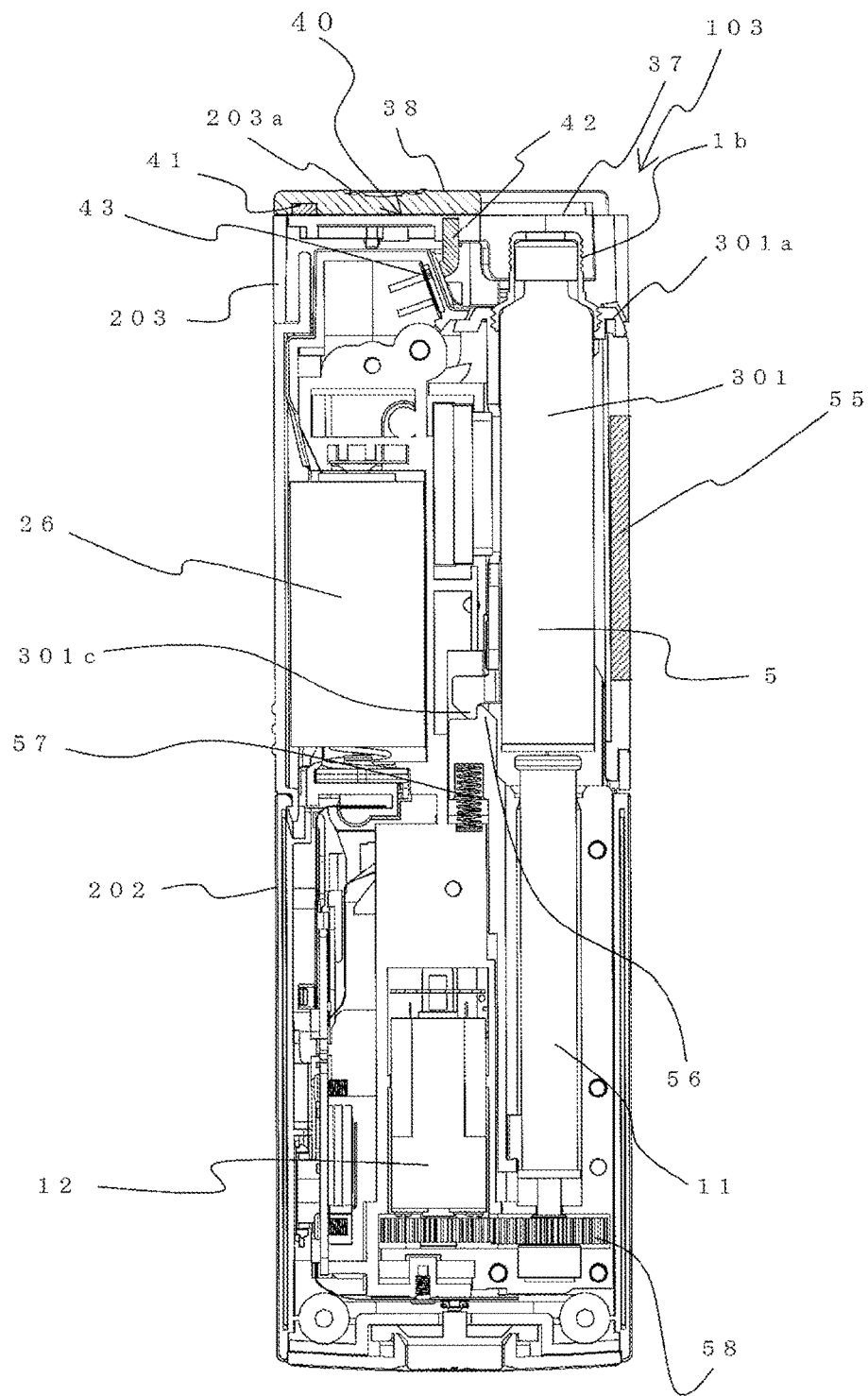
FIG. 19 is a cross section of the state when the cover of the pharmaceutical injection device shown in FIG. 18 has been opened up.
Figure 20:
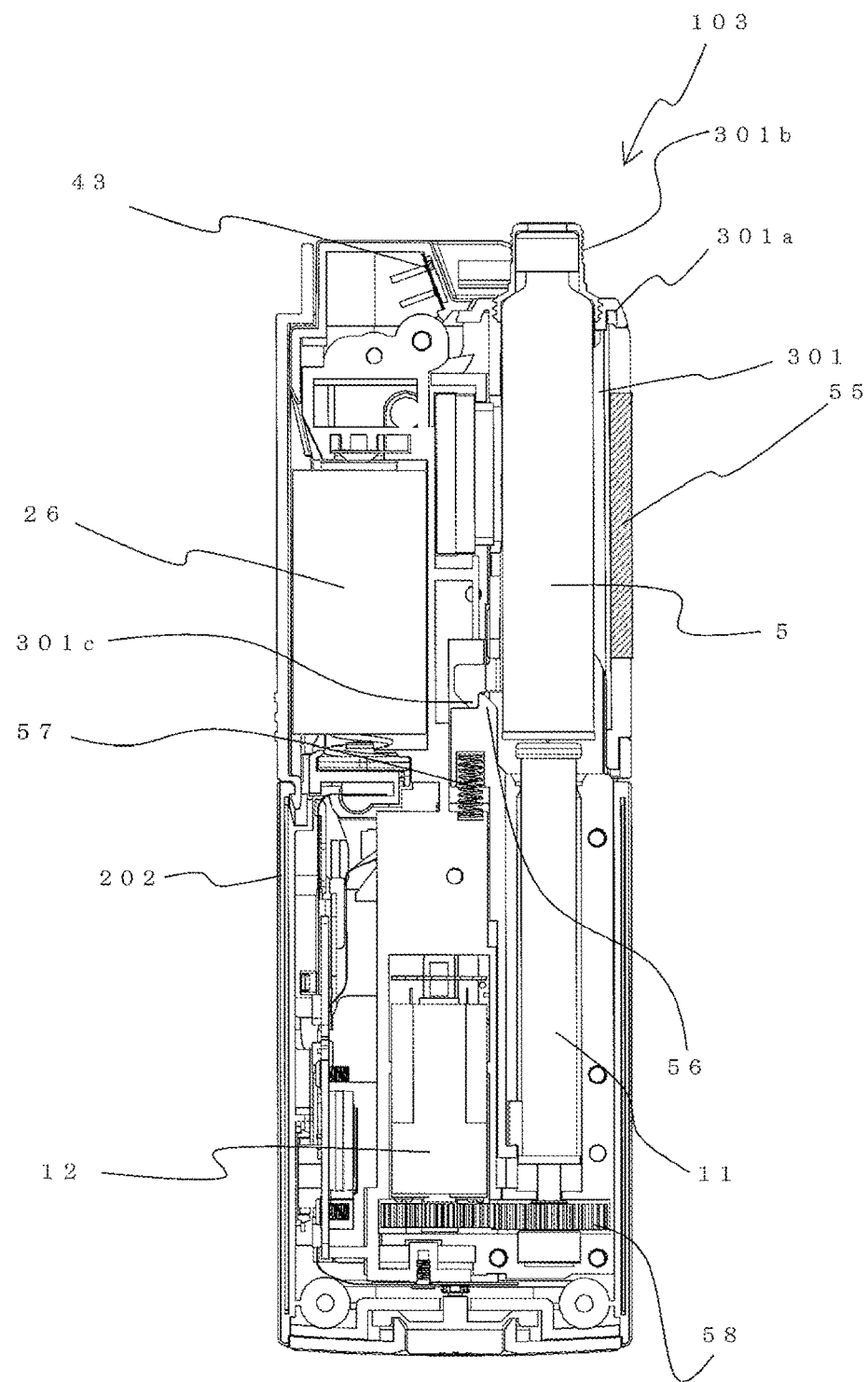
FIG. 20 is a cross section of the state when the cap of the pharmaceutical injection device shown in FIG. 19 has been removed.
Figure 21:
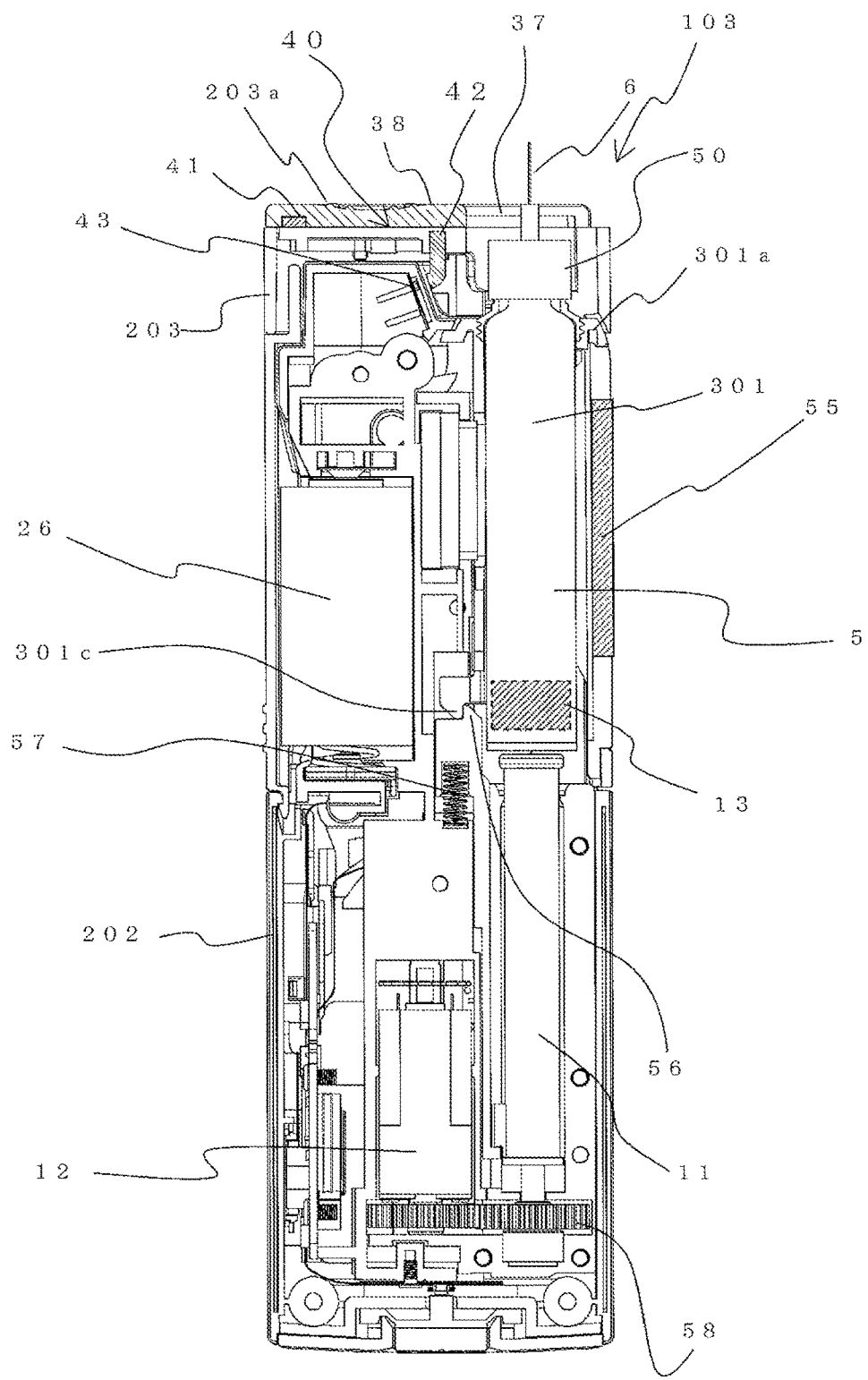
FIG. 21 is a cross section of the state when the injection needle of the pharmaceutical injection device shown in FIG. 18 has been mounted.

The configuration of Embodiment 3 will now be described through reference to FIGS. 17 to 23. FIG. 17 is an oblique view of the pharmaceutical injection device 103 in Embodiment 3. FIG. 18 shows the internal configuration of the pharmaceutical injection device 103 shown in FIG. 17. FIG. 19 shows the state when the cover 38 of the pharmaceutical injection device 103 shown in FIG. 18 has been opened up. FIG. 20 shows the state when the cap 203 of the pharmaceutical injection device 103 shown in FIG. 18 has been removed. FIG. 21 shows the state when the injection needle 6 has been mounted to the pharmaceutical injection device 103 shown in FIG. 19.

1. Configuration 1-1. Configuration of Pharmaceutical Injection Device 103

As shown in FIG. 17, the pharmaceutical injection device 103 in Embodiment 3 comprises a main case 202 that is substantially box-shaped and has a pharmaceutical syringe mounting component 301 on the inner distal end side. The configuration of the pharmaceutical injection device 103 in Embodiment 3 is substantially the same as in Embodiment 2, as shown in FIGS. 17 and 8.

As shown in FIGS. 17 and 20, a cap 203 is detachably provided to this distal end side of the main case 202. An opening 37 is formed as shown in FIG. 18 in the face 203a on the distal end side of the cap 203 shown in FIG. 17 (see to FIG. 9 in Embodiment 2). A cover 38 that is capable of sliding parallel to the face 203a is provided as shown in FIG. 17 in order to open and close this opening 37. Thus, the cover 38 is provided to the cap 203 that is detachably mounted to the main case 202.

Also, if we let the side on which the cap 203 is disposed be the front side or the distal end side of the pharmaceutical injection device 102, and the opposite side thereof be the rear end side, the display component 19 is provided toward the rear end side of the front face 202a of the main case 202. The pharmaceutical injection switch 17 is disposed on the distal end side of the display component 19 on the front face 202a, and selector switches 54a and 54b are provided on both sides of the pharmaceutical injection switch 17 in the width direction. The power switch 16 is disposed at the end of the front face 202a on the rear end side.

In FIG. 17, the air vent switch 18 is provided to an end face 202b that is on the left side when viewed with the front face 202a at the front.

1-2. Internal Configuration of Pharmaceutical Injection Device 103

As shown in FIG. 18, with the pharmaceutical injection device 103 in Embodiment 3, the pharmaceutical syringe mounting component 301 is formed so that the rear end side opens up from the main case 202, using a fulcrum 301a formed on the outside and the distal end side as a reference. In FIG. 18, the state in which the pharmaceutical syringe mounting component 301 is opened up is indicated by a two-dot chain line.

As shown in FIG. 18, the pharmaceutical syringe 5 is mounted to the pharmaceutical syringe mounting component 301 by opening up the pharmaceutical syringe mounting component 301 and inserting the pharmaceutical syringe 5 from below in FIG. 18 (see arrow B).

Also, the cover 38 of the opening 37 provided on the distal end side of the main case 202 is slid open as shown in FIGS. 18 and 19, and in this state, as shown in FIG. 21, the injection needle 6 is mounted on the distal end side of the pharmaceutical syringe mounting component 301, resulting in a state in which the injection needle 6 is mounted to the pharmaceutical syringe 5. As shown in FIG. 20, the cap 203 may be removed from the main case 202, the attachment component 50 of the injection needle 6 attached in this state to the needle mounting component 301b provided at the distal end of the pharmaceutical syringe mounting component 301, and the cap 203 attached to the main case 202 in a state in which the opening 37 is opened up.

A latched component 301c is formed at the rear end side on the inside of the pharmaceutical syringe mounting component 301, and when the pharmaceutical syringe mounting component 301 is closed, this is latched by the latching component 56 provided inside the main case 202. This latching component 56 is biased toward the distal end side by a spring 57, and this biasing force maintains the latched state of the latching component 56 and the latched component 301c.

Also, the piston 11 is provided to the rear of the pharmaceutical syringe 5 mounted in the body casing 202, just as in FIG. 2 in Embodiment 1. The piston 11 is linked to the piston drive motor 12 via a gear 58 disposed on the rear side of the piston 11, and the piston 11 is driven by the piston drive motor 12 toward the distal end side or the rear end side. This movement of the piston 11 to the distal end side pushes the gasket 13 (see FIG. 21) forward in the pharmaceutical syringe 5, and this pushes the pharmaceutical out of the pharmaceutical syringe 5 through the injection needle 6.

Specifically, when the piston drive motor 12 is driven, the piston 11 moves the gasket 13 forward, and as a result the pharmaceutical in the pharmaceutical syringe 5 is injected through the injection needle 6 into the body.

In Embodiment 3, since the cap 3 of Embodiment 1 is not provided, the protective cap 39 is mounted just as in Embodiment 2 (see FIG. 10). Removing the protective cap 39 from the injection needle 6 results in a state in which the injection needle 6 is exposed as shown in FIG. 21.

Therefore, the protective cap 39 is removed before the injection needle 6 pierces the skin, as shown in FIG. 21. Then, the injection needle 6 pierces the skin in the state in FIG. 21, and the pharmaceutical in the pharmaceutical syringe 5 is injected into the body from the injection needle 6.

In order to perform the above operation, the above-mentioned power switch 16, the pharmaceutical injection switch 17, the air vent switch 18, and the display component 19 are provided to the outer peripheral face of the main case 202 as discussed above. The charging terminal 20 is provided just as in Embodiment 1 to the outer peripheral face of the main case 202 of the pharmaceutical injection device 103 in Embodiment 3. This charging terminal 20 is the same as the one in FIG. 2, and is provided to the lower face side of the main case 202, so it is not depicted in FIGS. 17 to 21, but is depicted in FIG. 22.

1-3. Control Configuration of Pharmaceutical Injection Device 103

Figure 22:
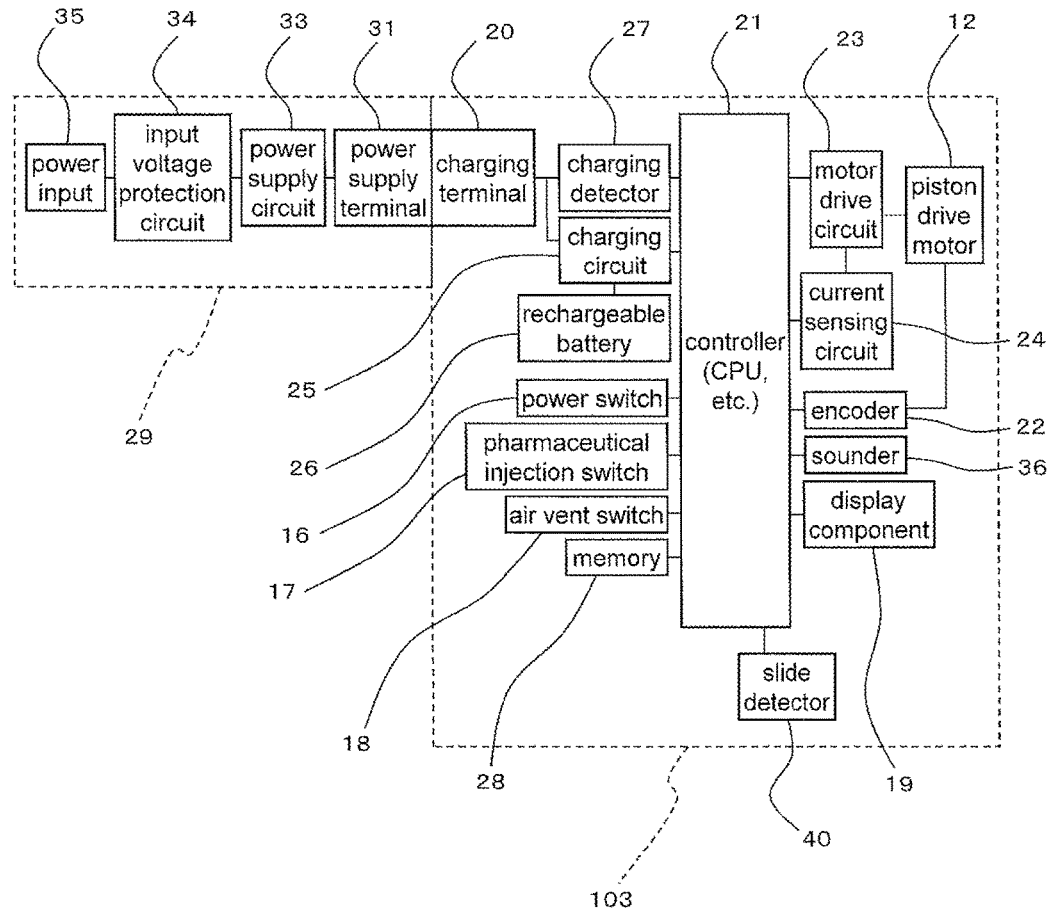
FIG. 22 is a control block diagram showing the simplified electrical configuration of the pharmaceutical injection device shown in FIG. 17 and its storage case.

FIG. 22 is a block diagram of the control configuration of the pharmaceutical injection device 103 in Embodiment 3.

The needle detector 8, the piston drive motor 12, the power switch 16, the pharmaceutical injection switch 17, the air vent switch 18, the display component 19, and the charging terminal 20 are connected to the controller 21 as shown in FIG. 22.

Of these, the piston drive motor 12 is connected to the controller 21 via the encoder 22.

The piston drive motor 12 is connected to the controller 21 via the motor drive circuit 23.

The motor drive circuit 23 is connected to the controller 21 via the current sensing circuit 24.

The charging terminal 20 is connected to the rechargeable battery 26 via the charging circuit 25.

The charging terminal 20 is connected to the controller 21 via the charging detector 27.

Similarly, the charging circuit 25 is also connected to the controller 21.

The memory 28, which stores control programs and the like, is connected to the controller 21.

Also, instead of the cap detector switch 10 used in Embodiment 1, the controller 21 is connected to a slide detector 40 for whether the cover 38 is open or closed.

1-4. Slide Detector 40

The slide detector 40 in Embodiment 3 has a configuration same as that in Embodiment 2, and will be described through reference to FIG. 14 in Embodiment 3, too.

As shown in FIGS. 14 and 18, the slide detector 40 comprises a magnet 41, a yoke 42, and a magnetic sensor 43. The magnet 41 is provided on the back face 38a of the cover 38, and is magnetized in a direction substantially perpendicular to the slide direction of the cover 38 (the back face 38a).

The yoke 42 is made of a soft magnetic material such as silicon steel or electromagnetic soft iron. The term "soft magnetic material" means a magnetic material whose magnetic permeability is high and whose coercivity is low. The yoke 42 is disposed such that one end 42a on the distal end side is opposite the magnet 41 in a state in which the cover 38 is closed (a state in which the opening 37 is covered by the cover 38), and the other end 42b on the rear end side is opposite the magnetic sensor 43. With this arrangement, the yoke 42 guides the magnetic flux generated by the magnet 41 when cover 38 is closed to the magnetic sensor 43, as indicated by the arrow P in the drawings.

The magnetic sensor 43 is connected to the controller 21 shown in FIG. 22, and outputs a signal to the controller 21 when a magnetic field is detected.

Specifically, as shown in FIG. 14, in the closed state of the cover 38, since one end of the yoke 42 is opposite the magnet 41, most of the magnetic flux from the magnet 41 flows to the magnetic sensor 43 that is disposed opposite the other end of the yoke 42, and as a result, the magnetic sensor 43 can detect that the cover 38 is closed.

The controller 21 detects that the output of the magnetic sensor 43 is in its on state, and determines that the cap 203 has been mounted to the main case 202, and that the cover 38 is closed.

1-5. Storage Case

The pharmaceutical injection device 103 in Embodiment 3 configured as above is similar to Embodiment 1 in that it is stored in the storage case 29 as shown in FIGS. 4 and 5, and the rechargeable battery 26 is charged during this storage. The storage case in Embodiment 3 differs only in the shape of the mounting recess 30, but its function is the same as that in Embodiment 1, so it will be described by referring to the storage case 29 of FIGS. 4 and 5.

More specifically, as shown in FIG. 4, the storage case 29 has the lid 32 and the placement component 53 in which is formed the mounting recess 30 in which the main case 202 of the pharmaceutical injection device 103 is mounted. The mounting recess 30 is formed to conform to the exterior shape of the pharmaceutical injection device 103 in a state in which the cap 203 has been mounted to the main case 202. When the main case 202 to which the cap 203 has been mounted is mounted in the mounting recess 30, just as in FIG. 6, the power supply terminal 31 provided to the mounting recess 30 comes into contact with the charging terminal 20 of the main case 202, and the rechargeable battery 26 is charged.

Again in Embodiment 3, in order to put the pharmaceutical injection device 103 in the storage case 29 for charging, the lid 32 in the state in FIG. 5 is configured to be closed and mate with the placement component 53 so as to cover the mounting recess 30 and the pharmaceutical injection device 103.

Also, the power supply terminal 31 is connected to the power input 35 via the power supply circuit 33 and the input voltage protection circuit 34, just as in FIG. 3. This power input 35 has a plug or the like that allows it to be plugged into an outlet, etc.

2. Operation

Figure 23A:
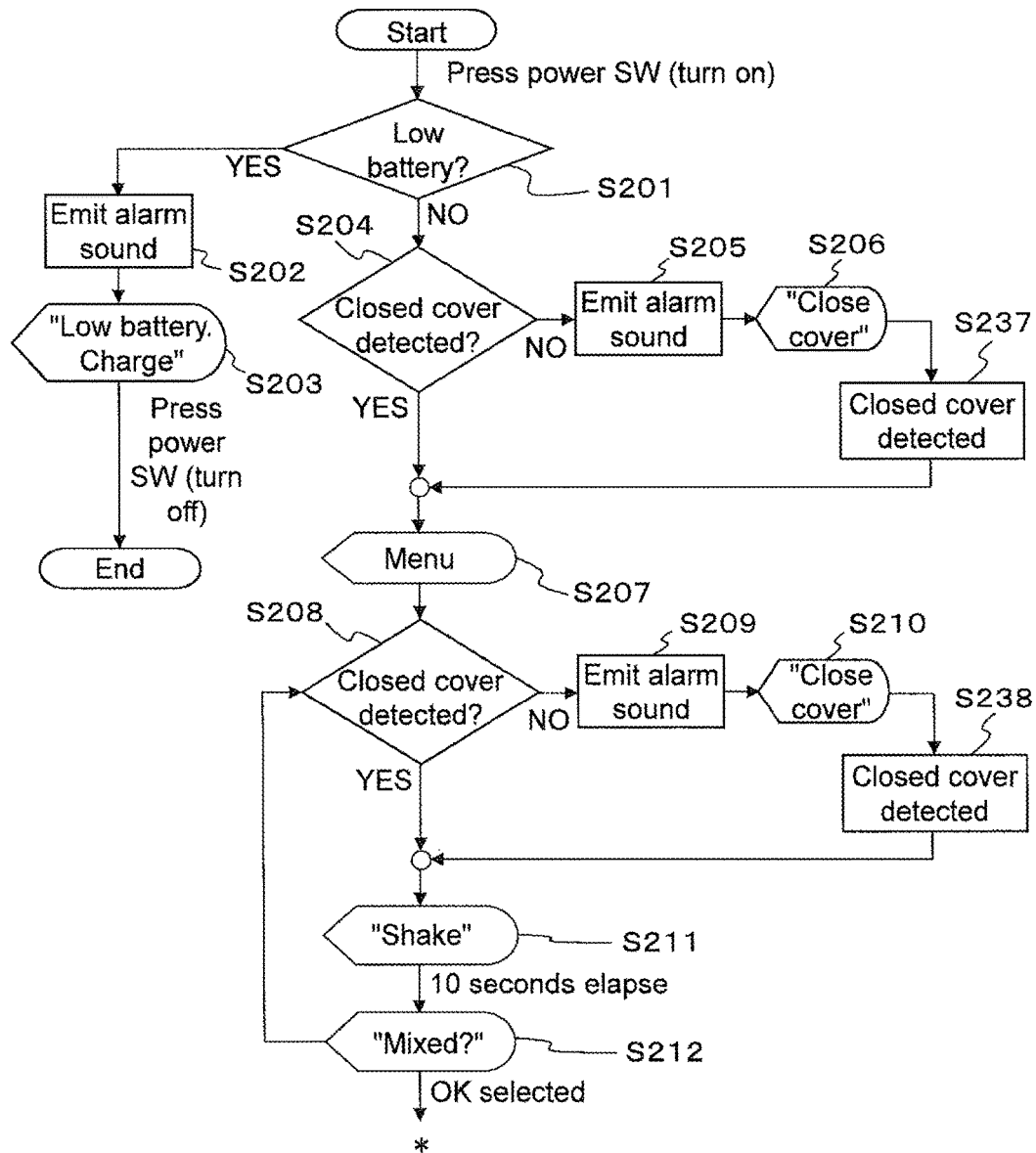
FIG. 23A is a flowchart of the operational control of the pharmaceutical injection device shown in FIG. 17.
Figure 23B:
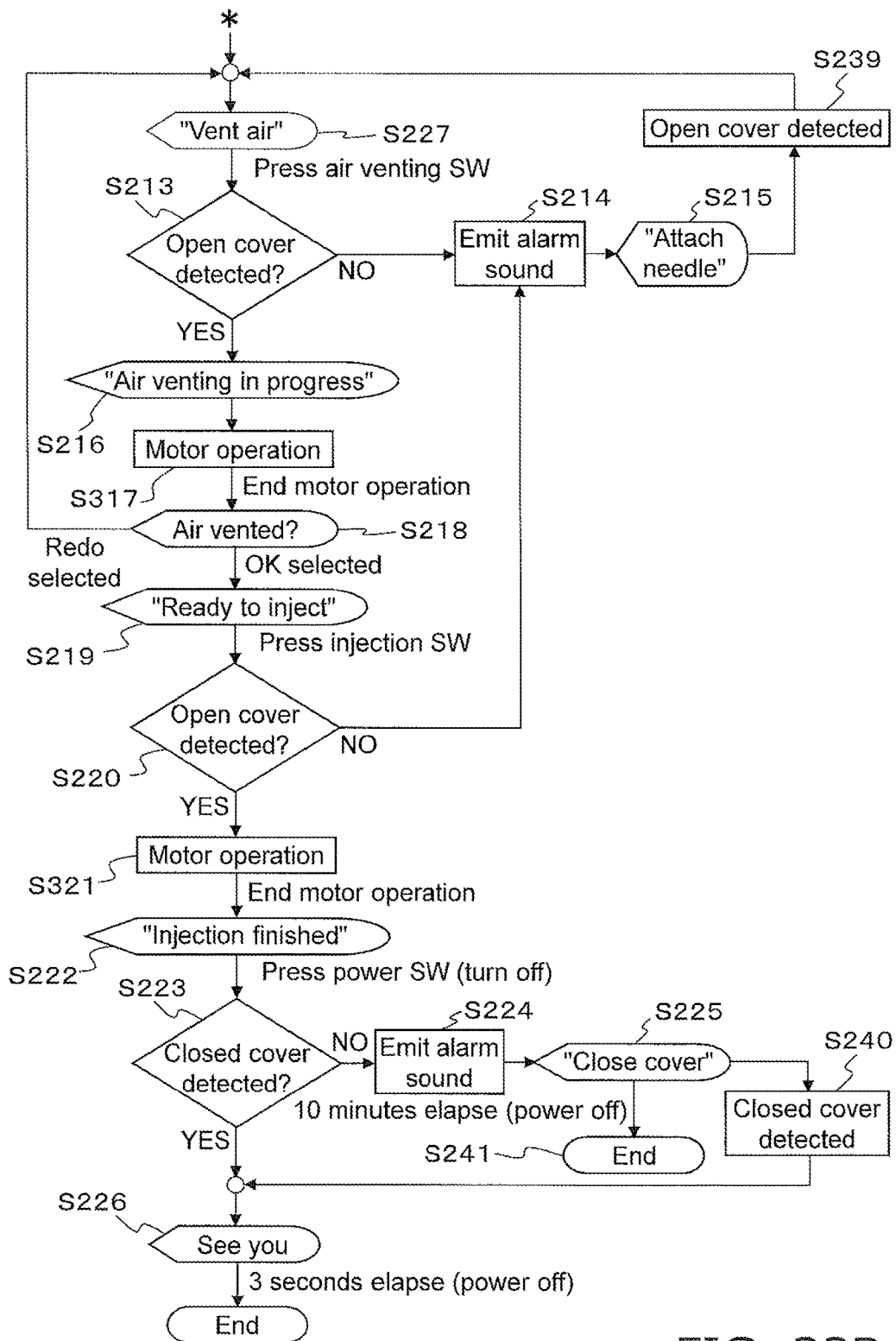
FIG. 23B is a flowchart of the operational control of the pharmaceutical injection device shown in FIG. 17.

FIGS. 23A and 23B are flowcharts illustrating the operation of the pharmaceutical injection device 103 in Embodiment 3.

In the above configuration, when the pharmaceutical is injected, the pharmaceutical injection device 103 is such that the pharmaceutical syringe mounting component 301 of the main case 202 is opened as shown in FIG. 18, and the pharmaceutical syringe 5 is mounted. The pharmaceutical syringe mounting component 301 is then closed. After this, the injection needle 6 covered by the protective cap 39 is mounted to the needle mounting component 301b of the pharmaceutical syringe mounting component 301.

Next, the protective cap 39 is pulled off as shown in FIG. 21 to expose the injection needle 6.

When the injection needle 6 covered by the protective cap 39 is mounted to the needle mounting component 301b of the pharmaceutical syringe mounting component 301, or when the protective cap 39 is pulled off to expose the injection needle 6, the cover 38 is slid to open up the opening 37. The mounting of the injection needle 6 may be performed through the opening 37 in a state in which the cap 203 has been attached, or may be performed in a state in which the cap 203 has been removed from the main case 202. If the injection needle 6 is mounted after the cap 203 has been detached, then the cap 203 is mounted to the main case 202 after this.

In this state, first the power switch 16 (labeled as power supply SW in FIGS. 23A and 23B) pushed down and put in its on state.

The controller 21 then senses the voltage of the rechargeable battery 26 via the charging circuit 25 (S201 in FIG. 23A).

Then, if the voltage of the rechargeable battery 26 is low, the controller 21 emits an alarm sound from the sounder 36 connected to the controller 21 as shown in FIG. 22 (S202 in FIG. 23A), and then a message prompting the user to charge the battery is displayed on the display component 19 (S203 of FIG. 23A).

More specifically, the display component 19 displays a message of "Low battery; charge." After the message is displayed, the power switch 16 is pressed by the user, the power supply is switched off, and control is ended.

When the voltage of the rechargeable battery 26 is at the proper level, first the slide detector 40 indirectly detects whether or not the injection needle 6 has been mounted to the pharmaceutical syringe 5 (S204 in FIG. 23A).

That is, in Embodiment 1 the fact that the injection needle 6 has been mounted to the pharmaceutical syringe 5 is directly detected by the needle detector switch 8, but in Embodiment 3 whether or not the injection needle 6 has been mounted to the pharmaceutical syringe 5 is detected indirectly by slide detector 40.

More precisely, in a state in which the cover 38 has been slid to open up the opening 37, the injection needle 6 is in a state of being mounted to the pharmaceutical syringe 5, so at this point the controller 21 indirectly determines that the injection needle 6 has been mounted to the pharmaceutical syringe 5.

The injection needle 6 is long enough to protrude beyond the opening 37. Therefore, in a state in which the injection needle 6 has been mounted to the pharmaceutical syringe 5, the cover 38 cannot be slid to close off the opening 37 because the injection needle 6 is in the way.

For this reason, in Embodiment 3, whether or not the injection needle 6 has been mounted to the pharmaceutical syringe 5 is detected indirectly by the slide detector 40 (S204 in FIG. 23A).

If it is determined that the injection needle 6 has been mounted, the controller 21 emits an alarm sound from the sounder 36 (S205 in FIG. 23A), then causes the display component 19 to display a message prompting the user to remove the injection needle 6 (S206 in FIG. 23A). More specifically, the controller 21 causes the display component 19 to display a direct indication of "Close cover." This display consequently (indirectly) instructs the user to remove the injection needle 6.

In S204 in FIG. 23A, if the cover 38 is determined to be closed, the controller 21 causes the display component 19 to display a menu (S207 in FIG. 23A). The control also proceeds to S207 if it is detected that the cover 38 is closed (S237) after the display in S206.

More specifically, in S207, the display shown in FIG. 16a is given. In FIG. 16a, "Inject," "Check history," and "Settings" are displayed as menus. An "Enter" key is displayed under these, and up and down arrow keys are displayed on the left and right of the display of the "Enter" key. The selector switches 54a and 54b are disposed under the up and down arrow keys, "Inject," "Check history," and "Settings" can be selected by pressing these selector switches 54a and 54b, and this action can be entered by pressing the pharmaceutical injection switch 17 disposed under the "Enter" key.

Here, when the inject is selected, the controller 21 checks the open or closed state of the cover 38 again (S208 in FIG. 23A).

More specifically, if the cover 38 is not closed, the controller 21 emits an alarm sound from the sounder 36 (S209 in FIG. 23A), then displays on the display component 19 a message prompting the user to remove the injection needle 6 (S210 in FIG. 23A). The controller 21 gives an indirect display of "Close cover" on the display component 19. This display indirectly tells the user to remove the injection needle 6.

In S208 of FIG. 23A, if the cover 38 is determined to be closed, the controller 21 displays "Shake" on the display component 19 (S211 in FIG. 23A). The control also proceeds to S211 when it is detected that the cover 38 is closed after the display in S210.

That is, better uniformity can be attained by stirring the pharmaceutical in the pharmaceutical syringe 5 mounted in the main case 202.

Then, after 10 seconds has elapsed, the controller 21 displays "Mixed?" on the display component 19. Here, specifically, in S212, the display shown in FIG. 16b is given. In FIG. 16b, along with the display of "Mixed?," menus of "OK" and "Redo" are displayed. Also, an "Enter" key is displayed below these displays, and up and down arrow keys are displayed on the left and right of the display of the "Enter" key. Either "OK" or "Redo" can be selected by using the pharmaceutical injection switch 17 and the selector switches 54a and 54b just as discussed above. In addition, a check window 55 (see FIG. 18), for example, is provided so that the user can check the state in the pharmaceutical syringe 5, and the user can look through the check window 55 to determine whether or not the pharmaceutical is mixed.

In S212, when the "OK" key displayed simultaneously with the display of "Mixed?" is operated pressed, the controller 21 causes the display component 19 to give a display prompting the user to vent the air (S227 in FIG. 23B). On the other hand, if "Redo" is selected, the control returns to S208, and "Shake" is displayed again.

At this point, if the air vent switch 18 shown in FIG. 17 is pressed, the controller 21 uses the slide detector 40 to detect whether or not the cover 38 is open (S213 in FIG. 23B).

That is, to vent the air, it is important that the injection needle 6 is mounted to the pharmaceutical syringe 5, and the mounting of the injection needle 6 to the pharmaceutical syringe 5 is detected indirectly from whether the cover 38 is open or closed.

Therefore, if the cover 38 is closed, the controller 21 emits an alarm sound from the sounder 36 (S214 in FIG. 23B), then displays on the display component 19 a message prompting the user to mount the injection needle 6 (S215 in FIG. 23B). The display at this point is a direct display of "Attach needle," but the display component 19 may instead display an image of the injection needle 6 as an indirect display. After the message of "Attach needle" is displayed in S215, if the slide detector 40 has detected that the cover 38 is open (S239), control returns to S227, and a message of "Vent air" is displayed again.

Then, if the mounting of the injection needle 6 to the pharmaceutical syringe 5 is indirectly detected in S213 in FIG. 23B from the fact that the cover 38 has been opened, the controller 21 causes the display component 19 to display "Air venting in progress" (S216 in FIG. 23B). After this display, the piston drive motor 12 is then driven to execute air venting. Then, when the air venting operation is complete, the piston drive motor 12 is stopped (S317 in FIG. 13). Here, with the pharmaceutical injection device 103 in Embodiment 3, since the needle insertion and withdrawal drive motor 15, the moving member 14, and so forth are not provided, only the piston drive motor 12 is operated, in contrast to S217 in Embodiment 2.

In Embodiment 3, as shown in FIG. 21, the injection needle 6 is in a state of protruding from the opening 37 of the main case 202.

If the distance by which the injection needle 6 protrudes from the opening 37 is thus increased, the needle insertion can be performed manually by the patient, healthcare worker, or the like by holding the main case 202.

In any case, in Embodiment 3, since the injection needle 6 protrudes from the opening 37 of the main case 202 in a state in which the injection needle 6 has been mounted to the pharmaceutical syringe 5 and the cover cannot be closed, the slide detector 40 can detected that the cover 38 is closed, or that the cover 38 is open. Thus, the injection needle 6 protrudes outward beyond the opening 37 in a state in which the injection needle 6 has been mounted to the pharmaceutical syringe 5, so when it is detected that the cover 38 is closed, the injection needle 6 can be determined not to have been mounted. That is, the mounting state of the injection needle 6 can be indirectly detected from whether the cover 38 is open or closed.

When this air venting is complete, the controller 21 causes the display component 19 to display "Air vented?" (S218 in FIG. 23B). More specifically, in S218, the display shown in FIG. 16c is given. In FIG. 16c, menus of "OK" and "Redo" are displayed along with the display of the "Air vented?" Also, an "Enter" key is displayed below these displays, and up and down arrow keys are displayed on the left and right of the display of the "Enter" key. Either "OK" or "Redo" can be selected by using the pharmaceutical injection switch 17 and the selector switches 54a and 54b just as discussed above. In addition, the user can visually confirm that pharmaceutical is coming out of the distal end of the injection needle 6, and can thereby determine whether or not the air has been vented.

At this point, when the OK key displayed on the display component 19 is pressed, the controller 21 causes the display component 19 to display "Ready to inject" (S219 in FIG. 23B). On the other hand, if the "Redo" key is pressed, control returns to S227 and the air venting operation is performed again.

When "Ready to inject" is displayed in S219, if the user places the opening 37 of the main case 202 against the pharmaceutical administration site (the skin), the injection needle 6 pierces the skin. The pharmaceutical injection switch 17 is then operated by the user.

Then, the controller 21 again checks whether the cover 38 is open or closed (S220 in FIG. 23B).

If the cover 38 is closed, the controller 21 issues an alarm sound from the sounder 36 (S214 in FIG. 23B), then causes the display component 19 to display a message prompting the user to mount the injection needle 6 (S215 in FIG. 23B).

In other words, it can be concluded that the injection needle 6 has not been mounted to the pharmaceutical syringe 5 from the fact that the cover 38 is closed, even though the pharmaceutical injection switch 17 has been operated in an attempt to perform pharmaceutical injection, so an alarm sound is emitted from the sounder 36 (S214 in FIG. 23B), and then a message prompting the user to mount the injection needle 6 is displayed on the display component 19 (S215 in FIG. 23B). If the slide detector 40 has detected that the cover 38 was opened after a message to "Attach needle" was displayed in S215 (S239), control returns to S227, and a message to "Vent air" is displayed again.

In contrast, if the cover 38 is opened in S220 in FIG. 23B, since it is indirectly determined that the injection needle 6 is mounted to the pharmaceutical syringe 5, at this point the injection needle 6 is in a state of having pierced the pharmaceutical administration site through the opening 37 in the main case 202, so the piston drive motor 12 is driven to inject the pharmaceutical inside the pharmaceutical syringe 5 into the body through the injection needle 6 (S321 in FIG. 13). Here, in Embodiment 3, unlike in Embodiment 2, the needle insertion and withdrawal drive motor 15 is not provided, so when the pharmaceutical injection switch 17 is operated, the piston drive motor 12 is then driven.

Once the injection is complete, the piston drive motor 12 is stopped, then the controller 21 causes the display component 19 to notify then user that the pharmaceutical injection has ended by displaying "Injection finished" (S222 in FIG. 23B).

The user, such as a patient or a healthcare worker, looks at this display of "Injection finished" and withdraws the injection needle 6 from the body.

When the power switch 16 is turned off in this state, the controller 21 confirms that the cover 38 is closed (S223 in FIG. 23B).

That is, the purpose of this step S223 is to determine whether or not the cover 38 has been closed after completion of the injection of the pharmaceutical. More specifically, when the pharmaceutical injection is complete, the user removes the injection needle 6 from the pharmaceutical syringe 5 and closes the cover 38 to store the pharmaceutical syringe 5 inside the main case 202.

Therefore, in S223, it can be determined that the injection needle 6 is still attached to the pharmaceutical syringe 5 by the cover 38 being not closed, so at this point an alarm sound is emitted from the sounder 36 (S224 in FIG. 23B). The controller 21 then causes the display component 19 to display the message "Close cover" (S225 in FIG. 23B). Thus, the user is indirectly prompted to remove the injection needle 6 by displaying "Close cover."

Also, in S223, if the slide detector 40 has detected that the cover 38 is closed, the controller 21 determines that the injection needle 6 has been properly removed from the pharmaceutical syringe 5, and therefore causes the display component 19 to display the message "See you" to end the operation (S226 in FIG. 23B).

In S225, if the slide detector 40 detects that the cover 38 is closed after displaying the message "Close cover" (S240), control proceeds to S226 and the message of "See you" is displayed.

Also, if it is not detected that the cover 38 is closed even after 10 minutes have elapsed since the display in S225, the power shut off and control is ended in order to reduce power consumption (S241).

3. Key Features (3-1)

As shown in FIG. 18, the pharmaceutical injection device 103 in Embodiment 3 comprises the main case 202, the piston 11, the piston drive motor 12 (an example of a driver), the power switch 16, the display component 19, and the controller 21. The main case 202 has the pharmaceutical syringe mounting component 301 to which the pharmaceutical syringe 5 is mounted. The piston 11 is provided movably with respect to the pharmaceutical syringe 5 mounted to the pharmaceutical syringe mounting component 301. The piston drive motor 12 drives the piston 11. The power switch 16 switches the power on and off. The display component 19 is provided to the main case 202. The slide detector 40 (an example of a needle detector) indirectly detects the mounting state of the injection needle 6. When the slide detector 40 indirectly detects that the injection needle 6 has been mounted in the switching off of the power switch 16, a first control is executed to cause the display component 19 to display a message that indirectly prompts the user to remove the injection needle 6 (S223, S225).

Thus, when the mounting state of the injection needle 6 is indirectly checked in the switching off of the power switch 16 and it is detected that the injection needle 6 has been mounted, a message prompting the user to remove the injection needle 6 is displayed.

Consequently, the user can be prompted to remove the injection needle 6 and put away the pharmaceutical injection device 103 in the storage case 29, so the user will be less likely to forget to remove the injection needle 6 when the device is put away.

Therefore, the user will also be less likely to reuse an injection needle 6 that has already been used.

(3-2)

As shown in FIG. 18, the pharmaceutical injection device 103 in Embodiment 3 further comprises the cap 203. The cap 203 is disposed on the distal end side of the pharmaceutical syringe mounting component 301, and is detachably attached to the main case 202. The cap 203 has the opening 37 formed opposite the distal end of the pharmaceutical syringe mounting component 301, and the cover 38 for opening and closing the opening 37. The injection needle 6 protrudes from the opening 37 in its mounted state. The slide detector 40 (an example of a needle detector) indirectly detects the mounting state of the injection needle 6 by detecting whether the cover 38 is open or closed.

In a state in which the injection needle 6 is mounted, the cover 38 cannot be closed since the injection needle 6 protrudes from the opening 37. Therefore, in a state in which the cover 38 is closed, can be concluded that the injection needle 6 has not been mounted.

Consequently, the fact that the injection needle 6 has not been mounted can be indirectly detected by detecting whether the cover 38 is open or closed, and the user will be less likely to forget to remove the injection needle 6.

(3-3)

As shown in FIG. 18, the pharmaceutical injection device 103 in Embodiment 3 is such that the slide detector 40 has the magnet 41, the yoke 42, and the magnetic sensor 43. The magnet 41 is provided to the cover 38. The yoke 42 is disposed inside the main case 202 so as to be opposite the magnet 41 in a state in which the cover 38 is closed. The magnetic sensor 43 is disposed opposite the yoke 42.

Consequently, the when cover 38 is closed, the magnetic flux generated by the magnet 41 is guided by the yoke 42 to the magnetic sensor 43, and the magnetic sensor 43 detects this magnetism. This makes it possible to detect that the cover 38 is closed.

4. Other Embodiments (A)

In this embodiment 3, in S223 and S225, control is ended after it is indirectly detected that injection needle 6 has been removed, but third control of detecting the charging state shown in S27, S28, and S29 in Embodiment 1 may be performed after the cover detection in S223.

In Embodiment 3, since the cover 38 is provided to the cap 203, the mounting of the cap 203 is detected along with the removal of the injection needle 6 by detecting that the cover 38 is closed. Therefore, it is not necessary to provide the second control shown in S23 and S25 in Embodiment 1. In other words, the second control shown in S23 and S25 in Embodiment 1 is already included in the first control shown in S223 and S225 in Embodiment 2.

(B)

In Embodiment 3, in S225 the user is indirectly prompted to remove the injection needle by displaying a message of "Close cover," but may instead be directly prompted to remove the injection needle with a message of "Remove needle."

(C)

The message of "Close cover" may indicate the closing of the cover not only directly, but also indirectly.

The indirect display for closing the cover 38 may also be a display of an image of closing the cover on the display component 19.

(D)

In Embodiment 3, the cap 203 is provided and the main case 202 is configured to be detachable, but it need not be detachable. In this case, the portion up to the cap 203 is formed as the main case 202, and the cover 38 is provided to the main case 202.

INDUSTRIAL APPLICABILITY

The pharmaceutical injection device of the present invention, and its storage case, are designed to prompt the user to use them properly, and are expected to find broad application to pharmaceutical injection devices for injecting various kinds of pharmaceutical.

REFERENCE SIGNS LIST

1 pharmaceutical syringe mounting component
2 main case
2s outer wall
3 cap
3a distal end opening
4 syringe cover
4a outer tube
4b needle mounting component
5 pharmaceutical syringe
6 injection needle
7 lever
7a distal end
7b protrusion
7c rear end
8 needle detector switch
9 lever
9a distal end
9b protrusion
9c rear end
10 cap detector switch
11 piston
12 piston drive motor (an example of a driver)
13 gasket
14 moving member
15 needle insertion and withdrawal drive motor
16 power switch
17 pharmaceutical injection switch
18 air vent switch
19 display component
20 charging terminal
21 controller
22 encoder
23 motor drive circuit
24 current sensing circuit 25 charging circuit
26 rechargeable battery
27 charging detector
28 memory
29 storage case
30 mounting recess
31 power supply terminal
32 lid
33 power supply circuit
34 input voltage protection circuit
35 power input
36 sounder
37 opening
38 cover
38a back face
39 protective cap
40 slide detector
41 magnet
42 yoke
42a one end
42b other end
43 magnetic sensor
50 attachment component
51 biasing component
52 biasing component
53 placement component
54 selector switch
54a, 54b selector switch
55 check window
56 latching component
57 spring
58 gear
101 pharmaceutical injection device
102 pharmaceutical injection device
103 pharmaceutical injection device
202 main case
202a front face
202b end face
203 cap
203a face
204 syringe cover
301 pharmaceutical syringe mounting component
301a fulcrum
301b needle mounting component
301c latched component

The invention claimed is:

1. A pharmaceutical injection device, comprising:
a main case that has a pharmaceutical syringe mounting component to which a pharmaceutical syringe is mounted;
a piston that is provided movably with respect to the pharmaceutical syringe mounted to the pharmaceutical syringe mounting component;
a driver that drives the piston;
a power switch that switches power on and off;
a display component that is provided to the main case;
a needle mounting component;
a needle detector that is provided to the main case and directly or indirectly detects whether an injection needle is mounted to the needle mounting component;
a cap that is removably attached to the main case so as to be disposed around an outer periphery of the pharmaceutical syringe in a state in which the pharmaceutical syringe is mounted to the pharmaceutical syringe mounting component;
a cap detector that detects whether the cap is attached to the main case; and
a controller that, after a user switches off the power switch:
executes a first control to display on the display component a message directly or indirectly prompting the user to remove the injection needle when mounting of the injection needle has been detected by the needle detector,
executes a second control to display on the display component a message prompting the user to mount the cap when mounting of the cap is not detected by the cap detector after execution of the first control, and
switches off the power if the injection needle is not removed and the cap detector does not detect mounting of the cap after a predetermined time.

2. The pharmaceutical injection device according to claim 1, wherein the needle detector detects whether the injection needle is mounted to the needle mounting component via a lever.

3. The pharmaceutical injection device according to claim 1, further comprising the injection needle,
wherein the pharmaceutical syringe is inserted into a syringe cover and thereby mounted to the pharmaceutical syringe mounting component, and the needle mounting component to which the injection needle is mounted is provided to a distal end of the syringe cover, and
the injection needle has an attachment component that is removably attached to the needle mounting component.

4. The pharmaceutical injection device according to claim 1, further comprising:
a charging terminal that is provided to the main case and is removably connected to an external power supply terminal; and
a charging detector that is connected via a charging circuit to the charging terminal and detects a charging state,
wherein the controller executes a third control to display on the display component a message prompting the user to connect the charging terminal to a power supply terminal when a state of non-charging to the charging circuit is detected by the charging detector after the second control.

5. A storage case in which the pharmaceutical injection device according to claim 4 is stored, said storage case comprising:
a mounting recess in which the main case of the pharmaceutical injection device is mounted; and
a power supply terminal that is provided to the mounting recess and is removably connected to the charging terminal.

6. The pharmaceutical injection device according to claim 1, wherein the predetermined time is at least 10 minutes.

7. A method for controlling a pharmaceutical injection device comprising a main case that has a pharmaceutical syringe mounting component to which a pharmaceutical syringe is mounted;
a piston that is provided movably with respect to the pharmaceutical syringe mounted to the pharmaceutical syringe mounting component;
a driver that drives the piston;
a power switch that switches power on and off;
a display component that is provided to the main case;
a needle mounting component;
a needle detector that is provided to the main case and directly or indirectly detects whether an injection needle is mounted to the needle mounting component;

a cap that is removably attached to the main case so as to be disposed around an outer periphery of the pharmaceutical syringe in a state in which the pharmaceutical syringe is mounted to the pharmaceutical syringe mounting component; and a cap detector that detects whether the cap is attached to the main case, said method comprising:

detecting a mounting state of the injection needle by the needle detector after the power switch is switched off;

displaying on the display component a message directly or indirectly prompting a user to remove the injection needle;

detecting whether the cap is attached to the main case after detecting the mounting state;

displaying on the display component a message directly or indirectly prompting a user to mount the cap; and switching off the power if the injection needle is not removed and the cap is not mounted after a predetermined period.

8. The method for controlling the pharmaceutical injection device according to claim 7, wherein the needle detector detects the mounting state of the injection needle via a lever.

9. The method for controlling the pharmaceutical injection device according to claim 7, wherein the pharmaceutical syringe is inserted into a syringe cover and thereby mounted to the pharmaceutical syringe mounting component, and the needle mounting component to which the injection needle is mounted is provided to a distal end of the syringe cover, and the injection needle has an attachment component that is removably attached to the needle mounting component.

10. The method for controlling the pharmaceutical injection device according to claim 7, wherein the pharmaceutical injection device further comprises:

a charging terminal that is provided to the main case and is removably connected to an external power supply terminal; and a charging detector that is connected via a charging circuit to the charging terminal and detects the charging state, and wherein the method further comprises displaying on the display component a message prompting the user to connect the charging terminal to a power supply terminal when a state of non-charging to the charging circuit is detected by the charging detector.

11. The method for controlling the pharmaceutical injection device according to claim 10, wherein the predetermined period is at least 10 minutes.

* * * * *